(12) United States Patent
Callizot

(10) Patent No.: US 11,951,113 B2
(45) Date of Patent: Apr. 9, 2024

(54) SYNERGESTIC COMBINATION COMPOSITION COMPRISING A STEROIDAL SAPONIN, A FIRST POLYPHENOLIC COMPOUND AND A SECOND POLYPHENOLIC COMPOUND

(71) Applicant: NEURALIA, Gardanne (FR)

(72) Inventor: Noëlle Callizot, Rognonas (FR)

(73) Assignee: NEURALIA, Gardanne (FR)

( * ) Notice: Subject to any disclaimer, the term of this patent is extended or adjusted under 35 U.S.C. 154(b) by 390 days.

(21) Appl. No.: 17/058,924

(22) PCT Filed: May 24, 2019

(86) PCT No.: PCT/EP2019/063548
§ 371 (c)(1),
(2) Date: Nov. 25, 2020

(87) PCT Pub. No.: WO2019/224388
PCT Pub. Date: Nov. 28, 2019

(65) Prior Publication Data
US 2021/0213034 A1 Jul. 15, 2021

(30) Foreign Application Priority Data

May 25, 2018 (EP) .................................... 18174223

(51) Int. Cl.
| | | |
|---|---|---|
| *A61K 31/58* | (2006.01) | |
| *A23L 33/105* | (2016.01) | |
| *A61K 31/192* | (2006.01) | |
| *A61K 36/48* | (2006.01) | |
| *A61K 36/894* | (2006.01) | |
| *A61K 36/8965* | (2006.01) | |
| *A61K 36/90* | (2006.01) | |
| *A61P 25/28* | (2006.01) | |

(52) U.S. Cl.
CPC ............ *A61K 31/58* (2013.01); *A23L 33/105* (2016.08); *A61K 31/192* (2013.01); *A61K 36/48* (2013.01); *A61K 36/894* (2013.01); *A61K 36/8965* (2013.01); *A61K 36/90* (2013.01); *A61P 25/28* (2018.01); *A61K 2236/33* (2013.01)

(58) Field of Classification Search
CPC .............. A23L 33/105; A61K 2236/33; A61K 2300/00; A61K 31/192; A61K 31/194; A61K 31/216; A61K 31/58; A61K 36/48; A61K 36/894; A61K 36/8965; A61K 36/90; A61P 25/16; A61P 25/28
See application file for complete search history.

(56) References Cited

U.S. PATENT DOCUMENTS

| | | |
|---|---|---|
| 6,258,386 B1 | 7/2001 | Xia et al. |
| 2017/0129915 A1 | 5/2017 | Tohda et al. |

FOREIGN PATENT DOCUMENTS

| | | | |
|---|---|---|---|
| CN | 105 832 743 A | 8/2016 | |
| EP | 1 066 042 B1 | 8/2006 | |
| EP | 2111864 A2 * | 10/2009 | ............. A23L 33/10 |
| EP | 3 106 160 A1 | 12/2016 | |
| EP | 3106160 A1 * | 12/2016 | ........... A61K 31/192 |
| EP | 3801556 B1 | 9/2022 | |
| JP | 2002507572 A | 3/2002 | |
| WO | 9948507 A2 | 9/1999 | |
| WO | 03/082893 A2 | 10/2003 | |
| WO | 2006/024545 A1 | 3/2006 | |
| WO | 2011/140655 A1 | 11/2011 | |
| WO | 2015163318 A1 | 10/2015 | |
| WO | 2016202453 A1 | 12/2016 | |
| WO | 2017/030167 A1 | 2/2017 | |
| WO | WO-2017030164 A1 * | 2/2017 | ............. F04D 11/00 |

OTHER PUBLICATIONS

Koh, Lab Anim Res 2016: 32(2), 105-115. (Year: 2016).*
Communication pursuant to Article 94(3) EPC dated Nov. 9, 2021 in corresponding European Application No. 19728601.6; 4 pgs.
Decision to grant a European patent pursuant to Article 97(1) EPC dated Aug. 11, 2022 in corresponding European Application No. 19728601.6; 2 pgs.
Transmission of the certificate for a European patent pursuant to Rule 74 EPC dated Sep. 20, 2022 in corresponding European Application No. 19728601.6; 1 pg.
International Search Report dated Aug. 29, 2019 in corresponding International Application No. PCT/EP2019/063548; 10 pages.
European Search Report dated Nov. 21, 2018 in corresponding European Application No. 18174223.0; 5 pages.
Ghasemzadeh et al., "Phytochemical constituents and biological activities of different extracts of Strobilanthes crispus (L.) Bremek leaves grown in different locations of Malaysia", BMC Complementary and Alternative Medicine, 2015, vol. 15 No. 422, 10 pages.
European Search Opinion dated Dec. 4, 2018 in corresponding European Application No. 18174223.0; 4 pages.
Communication under Rule 71(3) EPC including Intention to Grant dated Apr. 13, 2022 in corresponding European Application No. 19728601.6; 80 pages.

(Continued)

*Primary Examiner* — Jean P Cornet
(74) *Attorney, Agent, or Firm* — Maier & Maier, PLLC

(57) ABSTRACT

A combination composition including as active components, in synergistically effective amounts of (i) a steroidal saponin of natural or synthetic origin, a pharmaceutical acceptable salt thereof or a plant extract containing steroidal saponin, and (ii) at least a first polyphenolic compound selected from the group of hydroxycinnamic acids, flavonoids, hydroxybenzoic acids, and (iii) optionally, a second polyphenolic compound, wherein the second polyphenolic compound is hydroxycinnamic acids and its use in preventing, inhibiting, retarding or treating a subject suffering from a neurodegenerative disease or condition.

11 Claims, 34 Drawing Sheets

(56) References Cited

OTHER PUBLICATIONS

Imo et al., "Phytochemical Analysis of Gongronema latifolium Benth Leaf Using Gas Chromatographic Flame Ionization Detector"; International Journal of Chemical and Biomolecular Science, Jul. 20, 2015; vol. 1, No. 2, pp. 60-68.

* cited by examiner

| Potentially neuroprotective compounds | | | Range of studied concentrations of NSP02-14-E002 extract | | | | | | | |
|---|---|---|---|---|---|---|---|---|---|---|
| | Mw (g/mol) | Content (%) | 5 ng/mL | 50 ng/mL | 500 ng/mL | 2.5 µg/mL | 5 µg/mL | 15 µg/mL | 25 µg/mL | 30 µg/mL |
| protodioscin | 1049.199 | 0 | 0 | 0 | 0 | 0 | 0 | 0 | 0 | 0 |
| dioscin | 869.055 | trace | 0 | 0 | 0 | 0 | 0 | 0 | 0 | 0 |
| diosgenin | 414.63 | 0 | 0 | 0 | 0 | 0 | 0 | 0 | 0 | 0 |
| catechin | 290.26 | 0.71 | 122.3 pM | 1.2 nM | 12.2 nM | 61.2 nM | 122.3 nM | 3663.9 nM | 611.5 nM | 733.8 nM |

FIGURE 1 C

| Potentially neuroprotective compounds | | | Range of studied concentrations of NSP02-29-E001 extract | | | | | | | |
|---|---|---|---|---|---|---|---|---|---|---|
| | Mw (g/mol) | Content (%) | 1 ng/mL | 5 ng/mL | 10 ng/mL | 50 ng/mL | 100 ng/mL | 500 ng/mL | 1 µg/mL | 5 µg/mL |
| protodioscin | 1049.199 | 1.99 | 19.0 pM | 94.8 pM | 189.7 pM | 948.3 pM | 1.9 nM | 9.5 nM | 19.0 nM | 94.8 nM |
| dioscin | 869.055 | 5.78 | 66.5 pM | 332.5 pM | 665.1 pM | 3.3 nM | 6.6 nM | 33.3 nM | 66.5 nM | 332.5 nM |
| diosgenin | 414.63 | 0 | 0 | 0 | 0 | 0 | 0 | 0 | 0 | 0 |
| Afzelechin glucoside (catechin) | 290.26 | 0.33 | 7.6 pM | 37.8 pM | 75.6 pM | 378.1 pM | 756.2 pM | 3.8 nM | 7.6 nM | 37.8 nM |

FIGURE 2C

| Potentially neuroprotective compounds | | | Range of studied concentrations of NSP02-29-E002 extract | | | | | | |
|---|---|---|---|---|---|---|---|---|---|
| | Mw (g/mol) | Content (%) | 10 ng/mL | 50 ng/mL | 100 ng/mL | 500 ng/mL | 1 µg/mL | 5 µg/mL | 10 µg/mL | 20 µg/mL |
| protodioscin | 1049.199 | 5.59 | 532.8 pM | 2.7 nM | 5.3 nM | 26.7 nM | 53.3 nM | 266.4 nM | 532.8 nM | 1.1 µM |
| dioscin | 869.055 | 8.33 | 958.5 pM | 4.8 nM | 9.6 nM | 47.9 nM | 95.9 nM | 479.3 nM | 958.5 nM | 1.9 µM |
| diosgenin | 414.63 | 0 | 0 | 0 | 0 | 0 | 0 | 0 | 0 | 0 |
| Afzelechin glucoside (catechin) | 290.26 | 0.74 | 169.6 pM | 847.8 pm | 1.7 nM | 8.5 nM | 17.0 nM | 84.8 nM | 169.6 nM | 339.1 nM |

FIGURE 3 C

| Potentially neuroprotective compounds | | | Range of studied concentrations of NSP19-30-E002 extract | | | | | | | |
|---|---|---|---|---|---|---|---|---|---|---|
| | Mw (g/mol) | Content (%) | 10 ng/mL | 50 ng/mL | 100 ng/mL | 500 ng/mL | 1 µg/mL | 5 µg/mL | 10 µg/mL | 20 µg/mL |
| sarsasapogenin | 416.646 | 1.4 | 336.0 pM | 1.7 nM | 3.4 nM | 16.8 nM | 33.6 nM | 168.0 nM | 336.0 nM | 672.0 nM |
| caffeic acid | 180.159 | 0.046 | 25.5 pM | 127.7 pM | 255.3 pM | 1.3 nM | 2.6 nM | 12.8 nM | 25.5 nM | 54.1 nM |
| coumaric acid | 164.16 | 0.016 | 9.7 pM | 48.7 pM | 97.5 pM | 487.3 pM | 974.7 pM | 4.9 nM | 9.7 nM | 19.5 nM |

FIGURE 4C

| Potentially neuroprotective compounds | | | Range of studied concentrations of NSP Effect of CAT (1H pre-treatment) on neurite network of cortical neurons after glutamate injuries (40 µM)

* $p<0.05$ vs Glutamate condition, one-way ANOVA followed by Dunett's test

Effect of COU (1H pre-treatment) on survival of cortical neurons after glutamate injuries (40 µM)

* $p<0.05$ vs Glutamate condition, one-way ANOVA followed by Dunett's test

Effect of FA (1H pre-treatment) on survival of cortical neurons after glutamate injuries (40 µM)

* $p<0.05$ vs Glutamate condition, one-way ANOVA followed by Dunett's test

Effect of MIX GALLIC (1H pre-treatment) on survival of cortical neurons after glutamate injuries (40 μM)

* $p<0.05$ vs Glutamate condition, one-way ANOVA followed by Dunett's test

Effect of GALLIC (1H pre-treatment) on neurite network of cortical neurons after glutamate injuries (40 μM)

* $p<0.05$ vs Glutamate condition, one-way ANOVA followed by Dunett's test

SYNERGESTIC COMBINATION COMPOSITION COMPRISING A STEROIDAL SAPONIN, A FIRST POLYPHENOLIC COMPOUND AND A SECOND POLYPHENOLIC COMPOUND

FIELD

The present invention relates generally to a combination composition comprising a steroidal saponin, the preparation methods and usage thereof for treating neurodegenerative diseases. The invention relates more specifically to a combination composition for use preventing, inhibiting, retarding or treating a subject suffering from a neurodegenerative disease or condition.

BACKGROUND

Diosgenin and sarsasapogenin and their derivatives are the most frequently studied and showed neuroprotective effects. These two steroidal sapogenins are the most commonly encountered in Dioscoreaceae, Smilacaceae and Asparagaceae. In 2011, Ghayur et al. (Ghayur et al., Journal of Chinese Integrative Medicine: (2011) 9: 619-625) highlighted that diosgenin and phenolic compounds were possibly responsible for the anti-AChE activity in betel nut extract. Chiu et al. (Chiu et al., Am J Chin Med. (2011) 39:551-63) showed diosgenin (5-125 mg/kg) significantly improved the cognitive impairment and increased the activities of endogenous antioxidant enzymes in the brain of mice. Diosgenin also increased the activities of superoxide dismutase (SOD) and glutathione peroxidase (GSH-Px), and decreased the malondialdehyde (MDA) level in the brain of D-gal treated mice. Koh et al. (Lab Anim Res (2016) 32: 105-115) showed diosgenin inhibits neural cell death by reducing Aβ accumulation, upregulating SOD activity and suppressing lipid peroxidation. Diosgenin then recovers cerebral cholinergic function by enhancing AChE activity. Finally, diosgenin blocks neural cell death by accelerating NGF expression and stimulating the NGF receptor signaling pathway. Tohda (Tohda, Biol. Pharm. Bull. (2016) 39, 1569-1575) focused on the 1,25D3-MARRS pathway as a very critical target for anti-Alzheimer Disease (AD) therapy and demonstrated that the exogenous stimulator diosgenin activated this signaling pathway. Zhang et al. (Zhang et al., Naunyn-Schmiedeberg's Archives of Pharmacology (2017)) demonstrated that sarsasapogenin could suppress Aβ deposit and enhanced cell viability in high glucosecultured HT-22 cells, which was mediated likely through activation of PPARγ and subsequent downregulation of BACE1. The authors think sarsasapogenin has potent neuroprotective effects and may represent a new approach for the pharmacological treatment of diabetes-associated cognitive decline, probably Alzheimer's disease. Visanji et al. (Visanji et al., FASEB J. (2008) 22: 2488-2497) showed that smilagenin (an isomer of sarsasapogenin) has both neuroprotective and neurorestorative effects in vitro and in vivo. And this compound prevented and reversed neuronal damage induced by MPP+ in mesencephalic neurons and by MPTP in a mouse model of Parkinson's disease.

Polyphenols are among the most widespread class of metabolites in nature, and their distribution is almost ubiquitous. Phenylpropanoid family represents 20% of 200.000 existing secondary metabolites. This family contains the majority of the natural-occurring phenolics, such as hydroxycinnamic acid and its derivatives, flavonoids, coumarins or stilbenes. Among the hydroxycinnamic acids, caffeic acid, ferulic acid, chlorogenic acid, isoferulic acid and coumaric acid are known to have antioxidant activity.

Alzheimer's disease (AD) is a major public health problem due to its increasing prevalence, long duration, caregiver burden and high financial cost of care. In Alzheimer's disease, the most characteristic neuropathological changes are the formation of neurofibrillary tangles and neuritic plaques characterized by the presence of bundles of paired helical filaments that accumulate in the degenerating neurites and neuronal cell bodies. Classic neuritic plaques have a central dense core of β-amyloid peptide surrounded by a corona of dystrophic neurites (Esiri M M et al., J Neurol Neurosurg Psychiatry (1998) 65:29-33). Although the protein composition of the paired helical filaments is ill-defined, a number of microtubule-associated proteins have been implicated in these lesions. So, it has been reported that in the brains affected by Alzheimer's disease, the levels of microtubule-associated protein 2 (MAP 2) are usually decreased [Adlard P A, Vickers J C; Acta Neuropathol (2002) 103: 377-383; Hsia A Y et al.; Proc Natl Acad Sci USA (1999) 96: 3228-3233].

Currently there is no treatment for Alzheimer's disease. Current efforts to develop an effective treatment for AD are based upon the finding that Alzheimer's disease patients suffer from marked deficits in cholinergic neurotransmitter system, resulting in a deficiency in acetylcholine concentration in the central nervous system. Treatment approaches include precursors for acetylcholine synthesis, cholinergic agonists, acetylcholine release enhancers and acetylcholinesterase (AChE) inhibitors. To date, the most effective approach has been the use of AChE-inhibitors, such as tacrine, donepezil, and rivastigmine.

Previous studies showed that AD pathogenesis is triggered by the accumulation and deposition of toxic β-amyloid peptide (Aβ) in the central nervous system [Callizot et al., J. Neurosc. Res. (2013) 91(5):706-16]. Herbal medications targeting the mechanisms underlying Aβ-accumulation might be an effective approach to preventing the disease.

Parkinson's disease (PD) is the second most common neurodegenerative disorder in the United States. The predominant motor symptoms of PD including slow movement, resting tremor, rigidity and gait disturbance are caused by the loss of dopaminergic neurons in the substantia nigra (SN). Epidemiological studies suggest that the use of pesticides increases the risk of PD, possibly via reduced activity of complex I in the mitochondrial respiratory chain in the substantia nigra and result in the pathogenesis of PD. 1-methyl-4-phenyl-1,2,3,6-tetrahydropyridine (MPTP) and its derivative form (MPP+), a mitochondrial complex I inhibitor, has been widely used to produce toxin models of sporadic PD. This toxin is used to mimic in vitro PD [Visanji. et al., FASEB J. 2008; 22(7):2488-97].

The patent application EP 1 719 512 relates to the use of one or more active agents selected from sarsasapogenin and smilagenin in the preparation of a medicament for the treatment of a disease selected from Parkinson's disease, postural hypotension, autism, chronic fatigue syndrome, Myasthenia Gravis, Lambert Eaton disease, Gulf War Syndrome and occupational exposure to organophosphorus compounds. In particular, it was demonstrated effects of sarsasapogenin and smilagenin on the expression of m2 receptors on CHO cells, at concentrations ranging between 1 μmol/L and 10 μmol/L. However, such concentrations of 1 μmol/L or 10 μmol/L of sarsasapogenin are toxic for cortical neurons and for neuritic network.

The patent application US2008/118583 relates to a method for treating Parkinson's disease in a patient in need thereof comprising administering an effective amount of a synergistic nutraceutical composition, wherein said composition comprises: 21 mg of *Eleutherococcus senticosus,* 106 mg of Panax ginseng, 32 mg of *Rhodiola rosea,* 4 mg of *Schizandra chinensis,* 106 mg of *Astragalus membranaceus,* 106 mg of *Ganoderma lucidum,* 106 mg of *Uncaria tomentosa,* 21 mg of Coenzyme Q10, 21 mg of *Ginkgo biloba,* 64 mg of *Hydrocotyle asiatica,* 106 mg of *Radix polygalae,* 21 mg of *Silybum marianum,* 4 mg of *Smilax regelii,* 21 mg of *Tabebuia avellanedae,* 106 mg of Vitamin B1 and 106 mg of Vitamin E together with pharmaceutically acceptable excipients to said patient sufficient to alleviate said disease. However, the patent application US2008/118583 fails to disclose a specific combination composition comprising a steroidal saponin and a first polyphenolic compound and optionally a second polyphenolic compound, but solely a mixture of different plant extracts.

Hence, there is a need for new, effective composition comprising of the active compounds for preventing, inhibiting, retarding or treating a subject suffering from a neurodegenerative disease or condition, which can be administered with better treatments regimes and which can provide sufficient efficacy with improve patient tolerance, due to the low concentration of the active compounds.

SUMMARY

In this context, the inventors have developed a novel synergistically combination composition comprising a steroidal saponin and a first polyphenolic compound and optionally a second polyphenolic compound. Indeed, the inventors have shown for the first time that a steroidal sapogenin and polyphenolic compounds have synergistic effects when used in combination for the treatment of Alzheimer's disease. They investigated the neuroprotective effect of a plant extract of Dioscoreaceae, Asparagaceae, Smilacaceae and Fabaceae on rat primary cortical neurons injured with glutamate as in vitro model of AD. In light of the obtained results and an analytical analysis of the chemical profile of the extract, they identified three compounds potentially involved in the neuroprotective effect:diosgenin, caffeic acid and ferulic acid. The synergistic effect of these compounds was also investigated. The effect of said compounds was further investigated in a second in vitro model of AD which is β-amyloid peptide injured primary cortical neurons.

Therefore, one object of the present invention is to provide a combination composition for treatment of Alzheimer's disease and other central nervous system disorders and a preparation method thereof.

BRIEF DESCRIPTION OF THE DRAWINGS

FIG. 4C shows concentration of different compounds in dose of extract tested—NSP19-30-E002 (in grey, the range of active concentrations).

FIG. 5C shows concentration of different compounds in dose of extract tested—NSP20-31-E002 (in grey, the range of active concentrations).

DETAILED DESCRIPTION OF THE INVENTION

Figure 1:
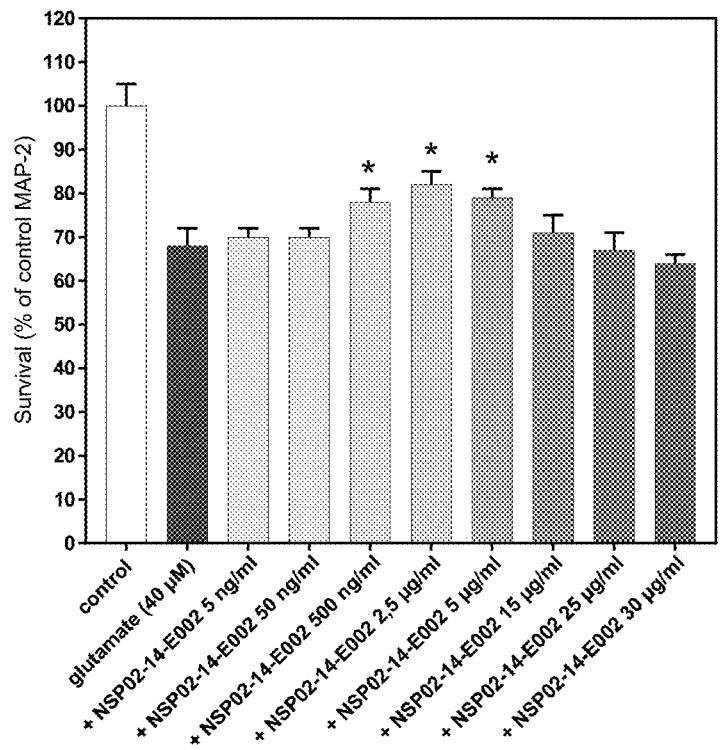
FIG. 1A and FIG. 1B illustrate the effect of Glutamate (40 µM, 20 min) in presence or absence of NSP02-14-E002 (different concentrations) on primary cortical neuron survival (FIG. 1A) and neurite network (FIG. 1B). Data were expressed as percentage of control as mean±SEM (100%=no glutamate). *$p<0.05$ vs glutamate (one way ANOVA followed by PLSD Fisher test).
FIG. 1C shows concentration of different compounds in dose of extract tested—NSP02-14-E002 (in grey, the range of active concentrations).
Figure 1:
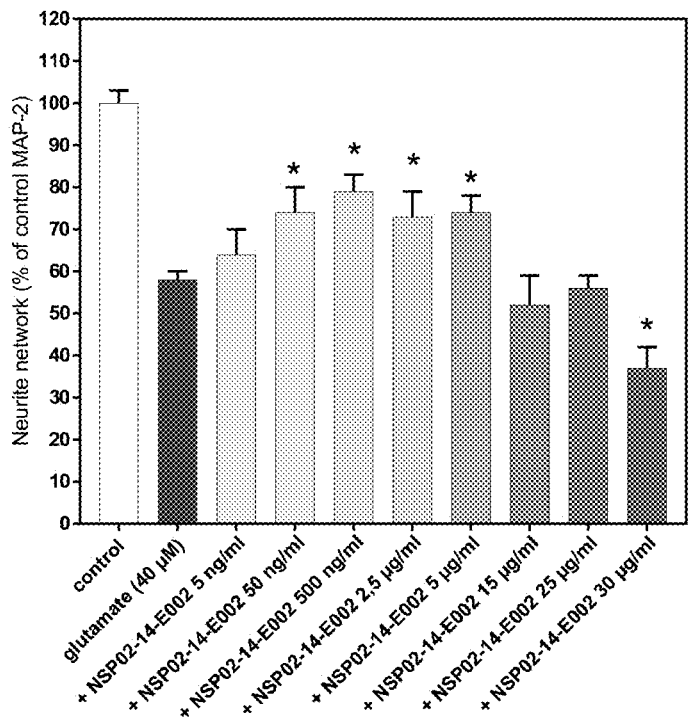

The present invention relates to a combination composition comprising as active components, in synergistically effective amounts of (i) a steroidal saponin of natural or synthetic origin, a pharmaceutical acceptable salt thereof or a plant extract containing steroidal saponin, and (ii) a first polyphenolic compound selected from the group consisting of: hydroxycinnamic acids, flavonoids, hydroxybenzoic acids, and optionally, (iii) a second polyphenolic compound, wherein the second polyphenolic compound is hydroxycinnamic acids.

According to the present invention, the term "combination composition" refers to a composition which comprises a mixture of at least two different active compounds.

According to the present invention, the term "active compound" refers to compound, which is medically or biologically active, and in particular to compound having neuroprotective activity.

According to the present invention, the term "synergistically" or "synergy" refers to the interaction of at least two or more active components so that their combined effect is greater than their individual effects.

The compounds present in the composition may exist as stereoisomer. The term "stereoisomer" as used herein refers to and includes isomeric molecules that have the same molecular formula but differ in positioning of atoms and/or functional groups in the space. The term "stereoisomer" includes enantiomers (where different isomers are mirror-images of each other) and diastereomers (where different isomers are not mirror-images of each other). The term "diastereomers" include isomers such as conformers, meso compounds, cis- trans (E-Z) isomers, and non-enantiomeric optical isomers.

According to the present invention, the steroidal saponin can be of natural or synthetic origin, pharmaceutical acceptable salt thereof or a plant extract containing the steroidal saponin.

Within the context of the present invention, the term "natural origin" refers to active steroidal saponin of plant origin.

Within the context of the present invention, the term "synthetic origin" refers to active steroidal saponin obtained by semisynthesis or hemisynthesis, for which the structure is similar or at least partly mimics the structure of active steroidal saponin of plant origin. Examples of synthetic steroidal saponin can include synthetic diosgenin, synthetic sarsasapogenin, synthetic sarsaponin, synthetic smilagenin, synthetic tigogenin, synthetic asparagin and synthetic laxogenin.

Within the context of the present invention, the term "plant extract" refers to extract of flowers, extract of leafs, extract of roots, extract of seeds. Plant extracts can be obtained from a plant family selected in the group consisting of Dioscoreaceae, Asparagaceae, Smilacaceae Fabaceae and a mixture thereof. Advantageously, plant extracts are obtained from Dioscoreaceae or Asparagaceae.

Within the context of the present invention, the term "pharmaceutical acceptable salt" refers to salts prepared from pharmaceutically acceptable non-toxic bases including inorganic bases and organic bases. Salts derived from inorganic bases include aluminium, ammonium, calcium, copper, ferric, ferrous, lithium, magnesium, manganic salts, manganese, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Quarternary ammonium salts such as N+(C1-4alkyl)4 are also included. Pharmaceutical acceptable salt refers also to salts prepared from pharmaceutically acceptable non-toxic acids including inorganic acids and organic acids. Salts derived from inorganic acids include bromhydrate, chlorhydrate, nitrate, phosphate, sulfate. Salts derived from pharmaceutically acceptable organic non-toxic acids include benzenesulfonate, citrate, ethanesulfonate, fumarate, gluconate, iodate, isethionate, maleate, methanesulfonate, methylene-bis-b-oxynaphtoate, oxalate, palmoate, salicylate, tartrate, theophyllinacetate and p-toluenesulfonate. The preparation of the pharmaceutically acceptable salts described above and other typical pharmaceutically acceptable salts is more fully described by Berge et al., "Pharmaceutical Salts,"/. Pharm. Set, 1977:66:1-19.

According to the present invention, the combination composition comprises a steroidal saponin, also called tetracyclic triterpenoids. The steroidal saponin of the present invention can be selected from the group consisting of diosgenin, sarsasapogenin, sarsaponin, smilagenin, tigogenin, laxogenin, their natural derivatives and mixtures thereof. According to the present invention, natural derivatives of steroidal saponin comprise heterosidic derivatives or substituted derivatives of the steroidal saponin. Within the context of the invention, the heterosidic derivatives or glycosides are molecules in which a sugar is bound to a functional group of the steroidal saponin. Among them may be cited dioscin or protodioscin. According to the invention the substituted derivatives are molecules in which a methoxy, group is bound to a functional group of the steroidal saponin via a O— bond. Among them may be cited icogenin, Me-protodioscin, dioscoreside E. In an advantageously embodiment of the invention, the steroidal saponin is selected from the group consisting of diosgenin, sarsasapogenin, smilagenin, their natural derivatives and mixtures thereof. In an advantageously embodiment of the invention, the steroidal saponin is diosgenin or its natural derivatives. In another advantageously embodiment of the invention, the steroidal saponin is sarsasapogenin or its natural derivatives. In another advantageously embodiment of the invention, the steroidal saponin is smilagenin or its natural derivatives.

According to the present invention, the combination composition comprises a first polyphenolic compound. The first polyphenolic compound of the invention can be selected from the group consisting of hydroxycinnamic acids, flavonoids and hydroxybenzoic acids. Advantageously, hydroxycinnamic acids are selected from the group consisting of α-cyano-4-hydroxycinnamic acid, caffeic acid, cichoric acid, cinnamic acid, chlorogenic acid, diferulic acids, isoferulic acids, coumaric acid, ferulic acid, sinapinic acid and a mixture of thereof. Advantageously, flavonoids are selected from the group comprising flavones for example luteolin and apigenin, flavonols for example quercetin, flavanol for example catechin, dihydroflavonols, flavanones, aurones, chalcones, and dihydrochalcones. Advantageously, hydroxybenzoic acids are selected from gallic acid, protocatechuic acid or syringic acid.

In a particular embodiment of the invention, the combination composition comprises a steroidal saponin and a first polyphenolic compound, wherein the steroidal saponin is selected from the group consisting of diosgenin, sarsasapogenin, smilagenin, their natural derivatives and mixtures thereof, and wherein the first polyphenolic compound is selected from the group consisting of catechin, caffeic acid and ferulic acid.

In one particular embodiment, the combination composition comprises a steroidal saponin and a first polyphenolic compound, wherein the steroidal saponin is diosgenin, its natural derivatives and mixtures thereof, and wherein the first polyphenolic compound is catechin. Advantageously, the combination composition comprising diosgenin its natural derivatives and mixtures thereof as steroidal saponin and catechin as first polyphenolic compound has a molar ratio which is comprised between 100/10 and 60/10.

In another particular embodiment, the combination composition comprises a steroidal saponin and a first polyphenolic compound, wherein the steroidal saponin is diosgenin, its natural derivatives and mixtures thereof, and wherein the first polyphenolic compound is caffeic acid. Advantageously, the combination composition comprising diosgenin its natural derivatives and mixtures thereof as steroidal saponin and caffeic acid as first polyphenolic compound has a molar ratio which is comprised between 0.03/5000 to 0.3/500. Advantageously, the combination composition comprising diosgenin its natural derivatives and mixtures thereof as steroidal saponin and caffeic acid as first polyphenolic compound has a molar ratio of 0.3/500.

In a particular embodiment of the invention, the combination comprises as active components, in synergistically effective amounts of diosgenin and caffeic acid, wherein the diosgenin is present at a concentration of from 0.01 pM to 0.5 pM, advantageously from 0.03 pM to 0.3 pM and the caffeic acid is present at a concentration of from 50 pM to 10 nM, advantageously from 500 pM to 5 nM.

In another particular embodiment, the combination composition comprises a steroidal saponin and a first polyphenolic compound, wherein the steroidal saponin is diosgenin, its natural derivatives and mixtures thereof, and wherein the first polyphenolic compound is ferulic acid. Advantageously, the combination composition comprising diosgenin, its natural derivatives and mixtures thereof as steroidal saponin and ferulic acid as first polyphenolic compound has a molar ratio which is comprised between 0.003/1000 to 0.3/1000. Advantageously, the combination composition comprising diosgenin its natural derivatives and mixtures thereof as steroidal saponin and ferulic acid as first polyphenolic compound has a molar ratio of 0.3/1000 or of 0.03/1000. In a particular embodiment of the invention, the combination comprises as active components, in synergistically effective amounts of diosgenin and ferulic acid, wherein the diosgenin is present at a concentration of from 0.01 pM to 0.5 pM, advantageously from 0.03 pM to 0.3 pM and the ferulic acid is present at a concentration of from 0.5 nM to 15 nM, advantageously from 1 nM to 10 nM.

In another particular embodiment, the combination composition comprises a steroidal saponin and a first polyphenolic compound, wherein the steroidal saponin is sarsasapogenin, its natural derivatives and mixtures thereof, and wherein the first polyphenolic compound is caffeic acid. Advantageously, the combination composition comprising sarsasapogenin, its natural derivatives and mixtures thereof as steroidal saponin and caffeic acid as first polyphenolic compound has a molar ratio which is comprised between 1/5000 to 1/50. Advantageously, the combination composition comprising sarsasapogenin, its natural derivatives and mixtures thereof as steroidal saponin and caffeic acid as first polyphenolic compound has a molar ratio of 1/50 or of 1/500.

In a particular embodiment of the invention, the combination comprises as active components, in synergistically effective amounts of sarsasapogenin and caffeic acid, wherein the sarsasapogenin is present at a concentration of from 0.5 pM to 15 pM, advantageously from 1 pM to 10 pM and the caffeic acid is present at a concentration of from 50 pM to 10 nM, advantageously from 500 pM to 5 nM.

In another particular embodiment, the combination composition comprises a steroidal saponin and a first polyphenolic compound, wherein the steroidal saponin is sarsasapogenin, its natural derivatives and mixtures thereof, and wherein the first polyphenolic compound is ferulic acid. Advantageously, the combination composition comprising sarsasapogenin its natural derivatives and mixtures thereof as steroidal saponin and ferulic acid as first polyphenolic compound has a molar ratio which is comprised between 0.1/1000 to 10/1000. Advantageously, the combination composition comprising sarsasapogenin, its natural derivatives and mixtures thereof as steroidal saponin and ferulic acid as first polyphenolic compound has a molar ratio of 10/1000 or of 1/1000.

In a particular embodiment of the invention, the combination comprises as active components, in synergistically effective amounts of sarsasapogenin and ferulic acid, wherein the sarsasapogenin is present at a concentration of from 0.5 pM to 15 pM, advantageously from 1 pM to 10 pM and the ferulic acid is present at a concentration of from 0.5 nM to 15 nM, advantageously from 1 nM to 10 nM.

In a particular embodiment of the invention, the combination composition may optionally comprise a second polyphenolic compound, which is hydroxycinnamic acids. Advantageously, the hydroxycinnamic acid used as second polyphenolic compound in the combination composition of the invention is selected from the group consisting of α-cyano-4-hydroxycinnamic acid, caffeic acid, cichoric acid, cinnamic acid, chlorogenic acid, diferulic acids, isoferulic acids, coumaric acid, ferulic acid, sinapinic acid and a mixture of thereof.

In a particular embodiment of the invention, the combination composition comprises as active components, in synergistically effective amounts of (i) a steroidal saponin of natural or synthetic origin, a pharmaceutical acceptable salt thereof or a plant extract containing steroidal saponin, and (ii) a first polyphenolic compound selected from the group consisting of hydroxycinnamic acids, flavonoids, hydroxybenzoic acids, and (iii) a second polyphenolic compound, wherein the second polyphenolic compound is hydroxycinnamic acids.

In an advantageously embodiment of the invention, the combination composition comprises as active components, in synergistically effective amounts of:
(i) a steroidal saponin of natural or synthetic origin, a pharmaceutical acceptable salt thereof or a plant extract containing steroidal saponin, and
(ii) a first polyphenolic compound, wherein the first polyphenolic compound is selected from catechin, caffeic acid and ferulic acid, and
(iii) a second polyphenolic compound, wherein the second polyphenolic compound is selected from caffeic acid and ferulic acid.

In a particular embodiment of the invention, the combination composition comprises as active components, in synergistically effective amounts of a steroidal saponin, a first polyphenolic compound and a second polyphenolic compound, wherein the steroidal saponin is selected from the group consisting of diosgenin, sarsasapogenin, smilagenin, their natural derivatives and mixtures thereof, wherein the first polyphenolic compound is selected from the group consisting of catechin, caffeic acid and ferulic acid and wherein the second polyphenolic compound is selected from caffeic acid and ferulic acid.

In an advantageously embodiment of the invention, the combination composition comprises as active components, in synergistically effective amounts of:
(i) a steroidal saponin of natural or synthetic origin, a pharmaceutical acceptable salt thereof or a plant extract containing steroidal saponin, and
(ii) caffeic acid as a first polyphenolic compound, and
(iii) ferulic acid as a second polyphenolic compound.

In an advantageously embodiment of the invention, the combination composition comprises as active components, in synergistically effective amounts of:
diosgenin or its natural derivatives or mixtures thereof as steroidal saponin, and
caffeic acid as first polyphenolic compound, and
ferulic acid as second polyphenolic compound.

In another advantageously embodiment of the invention, the combination composition comprises as active components, in synergistically effective amounts of:
sarsasapogenin or its natural derivatives or mixtures thereof as steroidal saponin, and
caffeic acid as first polyphenolic compound, and
ferulic acid as second polyphenolic compound.

In another advantageously embodiment of the invention, the combination composition comprises as active components, in synergistically effective amounts of:
smilagenin or its natural derivatives or mixtures thereof as steroidal saponin, and
caffeic acid as first polyphenolic compound, and
ferulic acid as second polyphenolic compound.

In a particular embodiment of the invention, the combination comprises as active components, in synergistically effective amounts of a steroidal saponin, a first polyphenolic compound and a second polyphenolic compound has a molar ratio steroid saponin/first polyphenolic compound/second polyphenolic compound which is comprised between from 0.01/1000/500 to 15/100000/20000. Advantageously, the molar ratio steroid saponin/caffeic acid/ferulic acid is comprised between from 0.03/5000/1000 to 10/50000/10000.

Advantageously, the molar ratio steroid saponin/first polyphenolic compound/second polyphenolic compound is comprised between from 0.03/5000/1000 to 0.3/5000/1000, where the steroidal saponin is diosgenin. Advantageously, the molar ratio diosgenin/caffeic acid/ferulic acid is selected among the following ratio: 0.03/5000/10000 or 0.3/5000/1000, or 0.3/5000/10000, or 0.3/50000/1000 or of 0.3/50000/10000.

In another particular embodiment of the invention, the combination comprises as active components, in synergistically effective amounts of a steroidal saponin, a first polyphenolic compound and a second polyphenolic compound has a molar ratio steroid saponin/first polyphenolic compound/second polyphenolic compound which is comprised between from 1/5000/1000 to 1/50000/10000, when the steroidal saponin is sarsasapogenin or smilagenin. Advantageously, the molar ratio steroid saponin/caffeic acid/ferullic acid is comprised between from 1/5000/1000 to 1/50000/10000, when the steroidal saponin is sarsasapogenin or smilagenin.

In a particular embodiment of the invention, the combination comprises as active components, in synergistically effective amounts of a steroidal saponin, a first polyphenolic compound and a second polyphenolic compound, wherein the steroidal saponin is present at a concentration of from 0.01 pM to 15 pM, the first polyphenolic compound is present at a concentration of from 1 nM to 100 nM, and the second polyphenolic compound is present at a concentration of from 0.5 nM to 20 nM. Advantageously, the steroidal saponin is selected among the group consisting of diosgenin, sarsasaponin, smilagenin, their natural derivatives or mixtures thereof.

In a particular embodiment of the invention, when the steroidal saponin is diosgenin, the steroidal saponin is present at a concentration of from 0.01 pM to 0.5 pM, advantageously between 0.015 pM to 0.45 pM, advantageously between 0.02 pM to 0.40 pM, advantageously between 0.025 pM to 0.35 pM, advantageously between 0.03 pM to 0.3 pM. In a particular embodiment, the concentration of the steroidal saponin in the combination composition of the invention is lower or equal to 0.3 pM, when the steroidal saponin is diosgenin.

In another particular embodiment of the invention, when the steroidal saponin is sarsasapogenin or smilagenin, the steroidal saponin is present at a concentration of from 0.5 pM to 15 pM, advantageously between 1 pM to 10 pM, advantageously between 1 pM to 9 pM, advantageously between 1 pM to 8 pM, advantageously between 1 pM to 7 pM, advantageously between 1 pM to 6 pM, advantageously between 1 pM to 5 pM, advantageously between 1 pM to 4 pM advantageously between 1 pM to 3 pM advantageously between 1 pM to 2 pM.

Advantageously, the first polyphenolic compound is present at a concentration of from 1 nM to 100 nM, advantageously between 1 nM to 95 nM, advantageously between 1 nM to 90 nM, advantageously between 1 nM to 85 nM, advantageously between 1 nM to 80 nM, advantageously between 1 nM to 75 nM, advantageously between 1 nM to 70 nM, advantageously between 1 nM to 65 nM, advantageously between 1 nM to 60 nM, advantageously between 1 nM to 55 nM, advantageously between 1 nM to 50 nM, advantageously between 2 nM to 50 nM, advantageously between 3 nM to 50 nM, advantageously between 4 nM to 50 nM, advantageously between 5 nM to 50 nM. In a particular embodiment, the concentration of the first polyphenolic compound in the combination composition of the invention is lower or equal to 50 nM. Advantageously, the first polyphenolic compound is caffeic acid.

Advantageously, the second polyphenolic compound is present at a concentration of from 0.5 nM to 20 nM, advantageously between 0.5 nM to 19 nM, advantageously between 0.5 nM to 18 nM, advantageously between 0.6 nM to 17 nM, advantageously between 0.6 nM to 16 nM, advantageously between 0.7 nM to 15 nM, advantageously between 0.7 nM to 14 nM, advantageously between 0.8 nM to 13 nM, advantageously between 0.8 nM to 12 nM, advantageously between 0.9 nM to 11 nM, advantageously between 0.9 nM to 10 nM, advantageously between 1 nM to 10 nM. In a particular embodiment, the concentration of the second polyphenolic compound in the combination composition of the invention is lower or equal to 10 nM. Advantageously, the first polyphenolic compound is ferulic acid.

Advantageously, the combination comprises as active components, a steroidal saponin, a first polyphenolic compound and a second polyphenolic compound, wherein the steroidal saponin is present at a concentration of from 0.03 pM to 15 pM, the first polyphenolic compound is present at a concentration of from 5 nM to 50 nM, and the second polyphenolic compound is present at a concentration of from 1 nM to 10 nM.

In an advantageously embodiment of the invention, the combination composition comprises as active components, in synergistically effective amounts of:
  diosgenin or its natural derivatives or mixtures thereof as steroidal saponin, wherein the diosgenin or its natural derivatives or mixtures thereof is present at a concentration of from 0.01 pM to 0.5 pM, advantageously between 0.03 pM and 0.3 pM and
  caffeic acid as first polyphenolic compound, wherein the caffeic acid is present at a concentration of from 1 nM to 100 nM, advantageously between 5 nM and 50 nM and
  ferulic acid as second polyphenolic compound, wherein the ferulic acid is present at a concentration of from 0.5 nM to 20 nM, advantageously between 1 nM and 10 nM.

In a particularly advantageous embodiment of the invention, the combination composition comprises:
  diosgenin or its natural derivatives or mixtures thereof at a concentration of 0.03 pM, and
  caffeic acid at a concentration of 5 nM, and
  ferulic acid at a concentration of 1 nM.

In a particularly advantageous embodiment of the invention, the combination composition comprises:
  diosgenin or its natural derivatives or mixtures thereof at a concentration of 0.03 pM, and
  caffeic acid at a concentration of 5 nM, and
  ferulic acid at a concentration of 10 nM.

In a particularly advantageous embodiment of the invention, the combination composition comprises:
  diosgenin or its natural derivatives or mixtures thereof at a concentration of 0.03 pM, and
  caffeic acid at a concentration of 50 nM, and
  ferulic acid at a concentration of 10 nM.

In a particularly advantageous embodiment of the invention, the combination composition comprises:
  diosgenin or its natural derivatives or mixtures thereof at a concentration of 0.03 pM, and
  caffeic acid at a concentration of 50 nM, and
  ferulic acid at a concentration of 1 nM.

In a particularly advantageous embodiment of the invention, the combination composition comprises:
  diosgenin or its natural derivatives or mixtures thereof at a concentration of 0.3 pM, and
  caffeic acid at a concentration of 5 nM, and
  ferulic acid at a concentration of 1 nM.

In a particularly advantageous embodiment of the invention, the combination composition comprises:
  diosgenin or its natural derivatives or mixtures thereof at a concentration of 0.3 pM, and
  caffeic acid at a concentration of 5 nM, and
  ferulic acid at a concentration of 10 nM.

In a particularly advantageous embodiment of the invention, the combination composition comprises:
   diosgenin or its natural derivatives or mixtures thereof at a concentration of 0.3 pM, and
   caffeic acid at a concentration of 50 nM, and
   ferulic acid at a concentration of 1 nM.

In a particularly advantageous embodiment of the invention, the combination composition comprises:
   diosgenin or its natural derivatives or mixtures thereof at a concentration of 0.3 pM, and
   caffeic acid at a concentration of 50 nM, and
   ferulic acid at a concentration of 10 nM.

In another embodiment of the invention, the combination composition comprises as active components, in synergistically effective amounts of:
   sarsasapogenin or its natural derivatives or mixtures thereof as steroidal saponin, wherein the sarsasapogenin or its natural derivatives or mixtures thereof is present at a concentration of from 0.5 pM to 15 pM, advantageously between 1 pM and 10 pM and
   caffeic acid as first polyphenolic compound, wherein the caffeic acid is present at a concentration of from 1 nM to 100 nM, advantageously between 5 nM and 50 nM and
   ferulic acid as second polyphenolic compound, wherein the ferulic acid is present at a concentration of from 0.5 nM to 20 nM, advantageously between 1 nM and 10 nM.

In another embodiment of the invention, the combination composition comprises as active components, in synergistically effective amounts of:
   smilagenin or its natural derivatives or mixtures thereof as steroidal saponin, wherein the smilagenin or its natural derivatives or mixtures thereof is present at a concentration of from 0.5 pM to 15 pM, advantageously between 1 pM and 10 pM and
   caffeic acid as first polyphenolic compound, wherein the caffeic acid is present at a concentration of from 1 nM to 100 nM, advantageously between 5 nM and 50 nM and
   ferulic acid as second polyphenolic compound, wherein the ferulic acid is present at a concentration of from 0.5 nM to 20 nM, advantageously between 1 nM and 10 nM.

Plant extracts, in particular Dioscoreaceae, Asparagaceae, Smilacaceae and Fabaceae may also be used as combination composition according to the invention. Thus, according to the present invention, said combination composition may be an aqueous or an organic mixture of said active components or a plant extract. Such extracts may be prepared by any technics known in the art in particular by ethanolic maceration assisted by ultrasound (UAE) or microwave (MAE). Advantageously, the plant extract is an ethanolic extract from a plant family selected in the group consisting of Dioscoreaceae, Asparagaceae, Smilacaceae and Fabaceae and a mixture thereof. According to the present invention, no extracts of *Rhodiola rosea, Uncaria tomentosa* or *Smilax regelii* are used for preparing the combination composition of the invention. In other terms, when the combination composition is obtained from plant extracts, the composition is free of *Rhodiola rosea, Uncaria tomentosa* or *Smilax regelii* extracts.

According to another aspect of the invention, the combination composition according to the invention may be used as a medicament or as a nutraceutical composition. The combination compositions according to the present invention may be prepared as pharmaceutical compositions, more particularly as neuroprotective pharmaceutical compositions. Such compositions may comprise the active compounds as defined above together with at least one pharmaceutically acceptable excipient.

The combination composition may be prepared as nutraceutical compositions comprising the active compounds as defined above together with at least one nutraceutically acceptable excipient.

Within the context of the invention, the term "pharmaceutically or nutraceutically acceptable excipient" refers to and includes compounds or materials used to facilitate administration of one or more compounds (or one or more active ingredients), for example, to increase the solubility of the compound. Typical, non-limiting examples of solid carriers include starch, lactose, dicalcium phosphate, sucrose, and kaolin. Typical, non-limiting examples of liquid carriers include sterile water, saline, buffers, non-ionic surfactants, and edible oils. In addition, various adjuvants commonly used in the art may also be included. These and other such compounds are described in literature, e.g., in the Merck Index (Merck & Company, Rahway, N.J.).

According to embodiments that involve administering to a subject in need of treatment a therapeutically effective amount of the combination composition as provided herein, "therapeutically effective" or "an amount effective to treat" or "pharmaceutically effective" denotes the amount of the combination composition of the invention needed to inhibit or reverse a disease condition (e.g., to treat the neurodegenerative disease). Determining a therapeutically effective amount specifically depends on such factors as toxicity and efficacy of the medicament. These factors will differ depending on other factors such as potency, relative bioavailability, patient body weight, severity of adverse side-effects and preferred mode of administration. Toxicity may be determined using methods well known in the art. Efficacy may be determined utilizing the same guidance. Efficacy, for example, can be measured by an increase of the survival of cortical neuron and neurite network of cortical neurons. A pharmaceutically effective amount, therefore, is an amount that is deemed by the clinician to be toxicologically tolerable, yet efficacious.

Dosage may be adjusted appropriately to achieve desired drug (e.g., combination composition of the invention) levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day may also be employed to achieve appropriate systemic levels of active compounds. Appropriate systemic levels can be determined by, for example, measurement of the patient's peak or sustained plasma level of the drug. "Dose" and "dosage" are used interchangeably herein.

In some embodiments, the amount of the combination composition administered to a subject in term of steroidal saponin is 1 to 20 mg/kg per week and in term of polyphenolic compound 1 to 100 mg/kg per week.

In some embodiments, the compositions provided are employed for in vivo applications. Depending on the intended mode of administration in vivo the compositions used may be in the dosage form of solid, semi-solid or liquid such as, e.g., tablets, pills, powders, capsules, gels, ointments, liquids, suspensions, or the like. Preferably, the compositions are administered in unit dosage forms suitable for single administration of precise dosage amounts. The compositions may also include, depending on the formulation desired, at least one pharmaceutically acceptable carrier or diluent, which are defined as aqueous-based vehicles commonly used to formulate pharmaceutical compositions for animal or human administration. The diluent is selected so as not to affect the biological activity of the active compounds present in the combination composition of the invention. Examples of such diluents are distilled water, physiological saline, Ringer's solution, dextrose solution, and Hank's solution. The same diluents may be used to reconstitute a lyophilized recombinant protein of interest. In addition, the pharmaceutical composition may also include other medicinal agents, pharmaceutical agents, carriers, adjuvants, nontoxic, non-therapeutic, non-immunogenic stabilizers, etc. Effective amounts of such diluent or carrier are amounts which are effective to obtain a pharmaceutically acceptable formulation in terms of solubility of components, biological activity, etc. In some embodiments the compositions provided herein are sterile.

Administration during in vivo treatment may be by any number of routes, including oral, parenteral, intramuscular, intranasal, sublingual, intratracheal, inhalation, ocular, vaginal, and rectal. Intracapsular, intravenous, and intraperitoneal routes of administration may also be employed. The skilled artisan recognizes that the route of administration varies depending on the disorder to be treated. For example, the combination composition herein may be administered to a subject via oral, parenteral or topical administration. In one embodiment, the combination composition herein are administered by per os.

The compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compositions in water soluble form. Additionally, suspensions of the active compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions. Alternatively, the active compositions may be in powder form for constitution with a suitable vehicle, e.g., sterile pyrogen-free water, before use.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. The component or components may be chemically modified so that oral delivery of the antibodies is efficacious. Generally, the chemical modification contemplated is the attachment of at least one molecule to the antibodies, where said molecule permits (a) inhibition of proteolysis; and (b) uptake into the blood stream from the stomach or intestine. Also desired is the increase in overall stability of the antibodies and increase in circulation time in the body. Examples of such molecules include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. Preferred for pharmaceutical usage, as indicated above, are polyethylene glycol molecules. For oral compositions, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the active compounds or by release of the biologically active material beyond the stomach environment, such as in the intestine.

For buccal administration, the compositions may take the form of tablets or lozenges formulated in conventional manner.

For administration by inhalation, the compositions for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compositions and a suitable powder base such as lactose or starch.

Also contemplated herein is pulmonary delivery. The compositions can be delivered to the lungs of a mammal while inhaling and traverses across the lung epithelial lining to the blood stream. Contemplated for use in the practice of this disclosure are a wide range of mechanical devices designed for pulmonary delivery of therapeutic products, including but not limited to nebulizers, metered dose inhalers, and powder inhalers, all of which are familiar to those skilled in the art.

Nasal delivery of a pharmaceutical composition disclosed herein is also contemplated. Nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextran.

The compositions may also be formulated in rectal or vaginal compositions such as suppositories or retention enemas, e.g., containing conventional suppository bases such as cocoa butter or other glycerides.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, capsules, powders, tablets, pills, coated tablets, (micro)capsules, suppositories, syrups, emulsions, suspensions, creams, gel, drops, patches, troches or preparations with protracted release of active compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

According to another object of the present invention, there is provided a combination composition such as described before for its use in preventing, inhibiting, retarding or treating neuronal degeneration in a subject suffering from a neurodegenerative disease or condition.

More particularly, the invention provides a combination composition for its use in preventing inhibiting, retarding or treating a subject suffering from a neurodegenerative disease or condition selected from the group consisting of: Alzheimer's disease (AD), senile dementia of AD type (SDAT), Parkinson's disease and all parkinsonian syndromes, Lewis body dementia, mild cognitive impairment (MCI), age-associated memory impairment (AAMI) and problem associated with ageing, non-cognitive neurodegeneration, non-cognitive neuromuscular degeneration, corticobasal ganglionic degeneration, multiple system atrophy, cerebral atrophy, olivopontocerebellar atrophy, supranuclear palsy, Niemann-Pick of type A disease, Pick diseases, traumatic neurodegeneration, Friedreich's ataxia, spinocerebellar ataxia type 2, Fahr's syndrome, Joubert syndrome, Huntington's disease, polyglutamine disease, dentatorubral atrophy, pallidoluysian atrophy, spinobulbar atrophy. myotonic dystrophy, Machado-Joseph's disease, amyotrophic lateral sclerosis (ALS), myasthenia gravis, Lambert Eaton's disease, infantile spinal amyotrophy or progressive spinal amyotrophy, motor-sensory neurodegeneration, multiple sclerosis, Guillain-Barre's syndrome, Charcot-Marie-Tooth disease (type 1 and 4), Progressive Multifocal Leukoencephalopathy (PML), leukodystrophic disesases, such as metachromatic leukodystrophy and adrenoleukodystrophy Alexander's disease, Krabbe's disease, Zellwegger's disease, Canavan disease, Pelizaeus-Merzbacher's syndrome, adrenomyeloneuropathy, neuropathies including hereditary neuropathy, diabetic neuropathy and anti-mitotic neuropathy. In a particular embodiment of the invention, the neurodegenerative disease or condition is selected from the group consisting of Alzheimer's disease (AD), senile dementia of AD type (SDAT) and Parkinson's disease.

Another subject of the invention relates to a method for preventing neurodegenerative disease or condition in patients in need of, comprising the administration to said patients of a pharmaceutical composition comprising a therapeutically effective amount of a steroidal sapogenin and a first polyphenolic compound and optionally a second polyphenolic compound as an active substance and at least one pharmaceutically acceptable carrier as defined above. In a particularly advantageous embodiment, the present invention relates to the use of a pharmaceutical composition comprising a therapeutically effective amount of a steroidal sapogenin and a first polyphenolic compound and optionally second polyphenolic compound as active compounds in the manufacture of a medicinal product intended for the prevention of neurodegenerative disease or condition.

In a particularly embodiment, the present invention relates to the use of a pharmaceutical composition comprising a therapeutically effective amount of diosgenin and catechin as active compounds in the manufacture of a medicinal product intended for the prevention of neurodegenerative disease or condition.

In a particularly embodiment, the present invention relates to the use of a pharmaceutical composition comprising a therapeutically effective amount of diosgenin and caffeic acid as active compounds in the manufacture of a medicinal product intended for the prevention of neurodegenerative disease or condition.

In a particularly embodiment, the present invention relates to the use of a pharmaceutical composition comprising a therapeutically effective amount of diosgenin and ferulic acid as active compounds in the manufacture of a medicinal product intended for the prevention of neurodegenerative disease or condition.

In a particularly embodiment, the present invention relates to the use of a pharmaceutical composition comprising a therapeutically effective amount of sarsasapogenin and caffeic acid as active compounds in the manufacture of a medicinal product intended for the prevention of neurodegenerative disease or condition.

In a particularly embodiment, the present invention relates to the use of a pharmaceutical composition comprising a therapeutically effective amount of sarsasapogenin and ferulic acid as active compounds in the manufacture of a medicinal product intended for the prevention of neurodegenerative disease or condition.

Another subject of the invention relates to a method for preventing neurodegenerative disease or condition in patients in need of, comprising the administration to said patients of a pharmaceutical composition comprising a therapeutically effective amount of a steroidal sapogenin and a first polyphenolic compound and a second polyphenolic compound as active compounds and at least one pharmaceutically acceptable carrier as defined above.

In a particularly advantageous embodiment, the present invention relates to the use of a pharmaceutical composition comprising a therapeutically effective amount of a steroidal sapogenin and a first polyphenolic compound and a second polyphenolic compound as active compounds in the manufacture of a medicinal product intended for the prevention of neurodegenerative disease or condition.

In a particularly advantageous embodiment, the present invention relates to the use of a pharmaceutical composition comprising a therapeutically effective amount of diosgenin, caffeic acid and ferulic acid as active compounds in the manufacture of a medicinal product intended for the prevention of neurodegenerative disease or condition.

In a particularly advantageous embodiment, the present invention relates to the use of a pharmaceutical composition comprising a therapeutically effective amount of sarsasapogenin, caffeic acid and ferulic acid as active compounds in the manufacture of a medicinal product intended for the prevention of neurodegenerative disease or condition.

In a particularly advantageous embodiment, the present invention relates to the use of a pharmaceutical composition comprising a therapeutically effective amount of smilagenin, caffeic acid and ferulic acid as active compounds in the manufacture of a medicinal product intended for the prevention of neurodegenerative disease or condition.

Another subject of the invention relates to a method for treating neurodegenerative disease or condition in patients in need of, comprising the administration to said patients of a pharmaceutical composition comprising a therapeutically effective amount of a steroidal sapogenin and a first polyphenolic compound and optionally a second polyphenolic compound as an active substance and at least one pharmaceutically acceptable carrier as defined above.

In a particularly advantageous embodiment, the present invention relates to the use of a pharmaceutical composition comprising a therapeutically effective amount of a steroidal sapogenin and a first polyphenolic compound and optionally second polyphenolic compound as active compounds in the manufacture of a medicinal product intended for the treatment of neurodegenerative disease or condition.

In a particularly embodiment, the present invention relates to the use of a pharmaceutical composition comprising a therapeutically effective amount of diosgenin and catechin as active compounds in the manufacture of a medicinal product intended for the treatment of neurodegenerative disease or condition.

In a particularly embodiment, the present invention relates to the use of a pharmaceutical composition comprising a therapeutically effective amount of diosgenin and caffeic acid as active compounds in the manufacture of a medicinal product intended for the treatment of neurodegenerative disease or condition.

In a particularly embodiment, the present invention relates to the use of a pharmaceutical composition comprising a therapeutically effective amount of diosgenin and ferulic acid as active compounds in the manufacture of a medicinal product intended for the treatment of neurodegenerative disease or condition.

In a particularly embodiment, the present invention relates to the use of a pharmaceutical composition comprising a therapeutically effective amount of sarsasapogenin and caffeic acid as active compounds in the manufacture of a medicinal product intended for the treatment of neurodegenerative disease or condition.

In a particularly embodiment, the present invention relates to the use of a pharmaceutical composition comprising a therapeutically effective amount of sarsasapogenin and ferulic acid as active compounds in the manufacture of a medicinal product intended for the treatment of neurodegenerative disease or condition.

Another subject of the invention relates to a method for treating neurodegenerative disease or condition in patients in need of, comprising the administration to said patients of a pharmaceutical composition comprising a therapeutically effective amount of a steroidal sapogenin and a first polyphenolic compound and a second polyphenolic compound as active compounds and at least one pharmaceutically acceptable carrier as defined above.

In a particularly advantageous embodiment, the present invention relates to the use of a pharmaceutical composition comprising a therapeutically effective amount of a steroidal sapogenin and a first polyphenolic compound and a second polyphenolic compound as active compounds in the manufacture of a medicinal product intended for the treatment of neurodegenerative disease or condition.

In a particularly advantageous embodiment, the present invention relates to the use of a pharmaceutical composition comprising a therapeutically effective amount of diosgenin, caffeic acid and ferulic acid as active compounds in the manufacture of a medicinal product intended for the treatment of neurodegenerative disease or condition.

In a particularly advantageous embodiment, the present invention relates to the use of a pharmaceutical composition comprising a therapeutically effective amount of sarsasapogenin, caffeic acid and ferulic acid as active compounds in the manufacture of a medicinal product intended for the treatment of neurodegenerative disease or condition.

In a particularly advantageous embodiment, the present invention relates to the use of a pharmaceutical composition comprising a therapeutically effective amount of smilagenin, caffeic acid and ferulic acid as active compounds in the manufacture of a medicinal product intended for the treatment of neurodegenerative disease or condition.

The invention will now be described in more detail in the following non-limiting examples and their accompanying FIGS. 1 to 20.

EXAMPLES

Example 1

Neuroprotective Effect on Alzheimer Disease (AD) Model

Glutamate excitotoxicity is responsible for neuronal death in acute neurological disorders including neurodegenerative disease. Loss of calcium homeostasis is a key mediator of glutamate-induced cell death. The inventors tested extracts from Verbena officinalis for their ability to prevent or reduce the toxic effects of glutamate on primary cortical neurons injured by glutamate.

1. Material and Methods 1.1. Preparation of Plant Extract

The extract by ethanolic maceration (EtOH 50-70% v/v) assisted by ultrasound (UAE), according to European Pharmacopeia 04/2008-0765, is named NSP02-14-E002 (*Dioscorea persimilis*), NSP02-29-E002 (*Dioscorea villosa*), NSP19-30-E002 (*Asparagus officinalis*) NSP20-31-E002 (*Smilax aspera*). The extract obtained by traditional decoction protocol (and optimized by micro-waves or not), is named NSP02-29-E001 (*Dioscorea villosa*).

The tetracyclic triterpenoids profile and the phenolic compounds profile of the extract are measured by two Ultra High Performance Liquid Chromatography (UHPLC) methods. The concentrations of the different compounds are calculated from these profiles. Samples and standards were analysed on an UHPLC-QqToF instrument (Dionex Ultimate 3000 equipped with RS Pump, autosampler and thermostated column compartment and UV diode array, Thermo Scientific®) hyphenated to an accurate mass spectrometer (MS) equipped with an ESI source (Impact II, Bruker Daltonics®). Mass spectra were acquired in positive and negative modes according to the physical and chemical characteristics of compounds. The first method allows to identify and to quantify the phenolic compounds (hydroxycinnamic acids, hydroxybenzoic acids, flavonoids, and substituted/heterosidic derivatives thereof); the second method is specific to tetracyclic triterpenoids. These methods are adaptation and transposition of many analytical methods [Tang Y, Yi T, Chen H, Zhao Z, Liang Z, Chen H., Phytochem Anal. (2013) 24:413-22; Narváez-Cuenca C E et al., Food Chemistry (2012) 130: 730-738; Ouyang H et al., Journal of Chromatographic Science (2016) 54(6): 1028-1036; Rehecho S et al., LWT—Food Science and Technology (2011) 44: 875-882; Quirantes-Piné R et al., Phytomedicine (2013) 20: 1112-1118; Brito A et al., Molecules (2014) 19: 17400-17421; Wang Y et al., J Anal Methods Chem. (2015) 2015:130873].

For hydroxycinnamic acids, hydroxybenzoic acids, flavonoids and substituted/heterosidic derivatives thereof:

Sample. Dissolve 0.0020 g of dry extract with 5 mL of MeOH and 5 mL of EtOH 60% (v/v) (Ethanol≥Lichrosolv®, gradient grade and Water—Chromasolv®, gradient grade; Sigma-Aldrich, Lyon, France). Homogenize with ultrasound during 5 min.

Standards (stock solution). Dissolve 0.0050 g of each standard with 5 mL of suitable mixture of solvent. Homogenize with ultrasound during 5 min. For catechin, rutin and for gallic, chlorogenic, caffeic, ferulic, rosmarinic and 4,5-dicaffeoylquinic acids [Extrasynthese, Genay, France; Sigma Aldrich, Lyon, France; Phytolab, Vestenbergsgreuth, Germany] add 0.5 mL of EtOH 60% and 0.5 mL of MeOH (Chromasolv®, gradient grade; Sigma-Aldrich, Lyon, France). Homogenize and add 1 mL of EtOH 60%, adjusted to 5 mL with 3 mL of Water. For luteolin-7-glucoside and vitexine (Extrasynthese, Genay, France): 0.5 mL EtOH 60%, 0.5 mL MeOH and 0.5 mL $H_2O$. Homogenize and add 0.5 mL of 2-PrOH, adjusted to 5 mL with 3 mL of Water. For apigenin (Sigma-Aldrich, Lyon, France): 3 mL of EtOH 60% and 2 mL of 2-PrOH. For luteolin and quercetin (Sigma-Aldrich, Lyon, France): 4 mL of EtOH 60% and 1 mL of 2-PrOH (hypergrade for LC-MS LiChrosolv®, Sigma-Aldrich, Lyon, France).

Introduce 50.0 µL of each stock solution in a 5 mL volumetric flask, add 300 µL of $H_2O$ and adjust at 5 mL with EtOH 60%.

Samples and standards were analysed with using a DIONEX Acclaim® C18 column (2.2 µm, 150×2.1 mm) at 50° C. The eluents used were water/formic acid (99.9:0.1, v/v) (eluent A) and acetonitrile/formic acid (99.9:0.1, v/v) (eluent B) (Chromasolv®, gradient grade and LC-MS ultragrade; Sigma-Aldrich, Lyon, France). The elution program (elution condition) was 0-6.5 min, 3-11% B; 6.5-17 min, 11-20% B; 17-22 min, 20-36% B; 22-29 min, 36-48% B; 29-32 min, 48-55% B; 32-35 min, 55-74% B; 35-37 min, 74-90% B; 37-40 min, 90% B; 40-40.5 min, 90-3% B; 40.5-42 min, 3% B. The flow rate was 380 µL/min; DAD detection was 240 and 280 nM; MS detection was in the negative ion mode, with a source voltage of 3.5 kV, and an ion transfer tube temperature of 350° C. A full-scan mass spectrum over a range of m/z values of 50-1500 was recorded; injection volume was 2 µL.

For tetracyclic triterpenoids and derivatives thereof:

Sample. Dissolve 0.0020 g of dry extract with 5 mL of MeOH and 5 mL of EtOH 60% (v/v). Homogenize with ultrasound during 5 min.

Standards (stock solution). Dissolve 0.0050 g of each standard with 5 mL of suitable mixture of solvent. Homogenize with ultrasound during 5 min. For protodioscin, dioscin, diosgenin and sarsasapogenin (Selleckchem—Euromedex, Souffelweyersheim, France) add 5 mL of MeOH and homogenize with ultrasound during 5 min.

Introduce 500.0 µL of each stock solution in a 5 mL volumetric flask and adjust at 2.0 mL with 0.5 mL of MeOH and 1.0 mL of EtOH 60%.

Samples and standards were analysed with using a DIONEX Acclaim® C18 column (2.2 µm, 150×2.1 mm) at 50° C. The eluents used were water/formic acid (99.9:0.1, v/v) (eluent A) and acetonitrile/formic acid (99.9:0.1, v/v) (eluent B). The elution program (elution condition) was 0-1 min, 10% B; 1-14 min, 10-90% B; 14-16.5 min, 90-95% B; 16.5-20.5 min, 95% B; 20.5-21 min, 95-10% B; 21-25 min, 10% B. The flow rate was 450 µL/min; DAD detection was 210 nM; MS detection was in the negative ion mode, with a source voltage of 3.5 kV, and an ion transfer tube temperature of 350° C. A full-scan mass spectrum over a range of m/z values of 50-1500 was recorded; injection volume was 2 µL.

1.2. Cell Model

Rat cortical neurons were cultured as described by Singer et al., (J. Neuroscience, (1999), 19(7), 2455-2463) and Callizot et al. (J. Neurosc., (2013), Res. 91(5), 706-716).

Pregnant females (Wistar; JanvierLabs, St Berthevin, France) at 15 days of gestation were killed by cervical dislocation. Foetuses were collected and immediately placed in ice-cold L15 Leibovitz medium (Pan Biotech, Aidenbach, Germany) with a 2% penicillin (10,000 U/ml) and streptomycin (10 mg/ml) solution (PS; Pan Biotech, Aidenbach, Germany) and 1% bovine serum albumin (BSA; Pan Biotech, Aidenbach, Germany). Cortex was treated for 20 min at 37° C. with a trypsin-EDTA (Pan Biotech, Aidenbach, Germany) solution at a final concentration of 0.05% trypsin and 0.02% EDTA. The dissociation was stopped by addition of Dulbecco's modified Eagle's medium (DMEM) with 4.5 g/liter of glucose (Pan Biotech, Aidenbach, Germany), containing DNAse I grade II (final concentration 0.5 mg/ml; Pan Biotech, Germany) and 10% fetal calf serum (FCS; Invitrogen, Cergy Pointoise, France). Cells were mechanically dissociated by three forced passages through the tip of a 10-ml pipette. Cells were then centrifuged at 515 g for 10 min at 4° C. The supernatant was discarded, and the pellet was resuspended in a defined culture medium consisting of Neurobasal medium (Invitrogen, Cergy Pointoise, France) with a 2% solution of B27 supplement (Invitrogen, Cergy Pointoise, France), 2 mmol/liter of L-glutamine (Pan Biotech, Aidenbach, Germany), 2% of PS solution, and 10 ng/ml of brain-derived neurotrophic factor (BDNF; Pan Biotech, Aidenbach, Germany). Viable cells were counted in a Neubauer cytometer, using the trypan blue exclusion test. The cells were seeded at a density of 30,000 per well in 96-well plates precoated with poly-L-lysine (Corning Biocoat, Tewksbury, USA) and were cultured at 37° C. in an air (95%)-CO2 (5%) incubator. The medium was changed every 2 days. The cortical neurons were intoxicated with glutamate solutions (see below) after 13 days of culture.

1.3. Glutamate Exposure

On day 13, glutamate (Sigma Aldrich, Lyon, France) was added into cell culture to a final concentration of 40 µM diluted in control medium in presence or absence of test compounds for 20 min. After 20 min, the cells were washed-out and new fresh medium containing or not NSPXX-E2 or NSPXX-E1 extracts was added for 48 h additional time.

1.4. Survival Evaluation

After 48 hours of glutamate intoxication, cells were fixed by a cold solution of ethanol (95%, Sigma) and acetic acid (5%, Sigma) for 5 min at −20° C. After permeabilization with 0.1% of saponin (Sigma), cells were incubated for 2 h with mouse monoclonal antibody anti microtubule-associated-protein 2 (MAP-2; Sigma) at dilution of 1/400 in PBS (Pan biotech) containing 1% foetal calf serum (Invitrogen) and 0.1% of saponin.

This antibody was revealed with Alexa Fluor 488 goat anti-mouse IgG (Invitrogen) at the dilution of 1/400 in PBS containing 1% foetal calf serum and 0.1% of saponin for 1 h at room temperature.

1.5. Technical and Statistical Analysis 1.5.1. Neurite Network Length Assessment:

For each condition 6 wells were assessed, 30 pictures per well were taken using MetaXpress (molecular device) with 20× magnification (30 pictures at X20 representing ~80% of the total well surface), to assess neurite network (MAP-2 staining). Analysis of picture was done using MetaXpress custum module editor software (molecular device), the total neurite length per picture was recorded). A mean neurite length of the ten pictures was automatically calculated per well, then one data was provided per well (total of 6 raw data were provided per condition).

1.5.2. Neuron Survival Assessment:

For each condition 6 wells were assessed, 30 pictures per well were taken using MetaXpress (molecular device) with 20× magnification to assess cell bodies (MAP-2 staining). Analysis of picture was done using MetaXpress custum module editor software (molecular device), the number of neurons per picture was recorded. A mean of neuron number of the ten pictures was automatically calculated per well, then one data was provided per well (total of 6 raw data were provided per condition).

1.6. Statistical Analysis

All values were expressed as mean+/−s.e.mean. Data were expressed in percentage of control conditions (no intoxication, no glutamate=100%) in order to express the glutamate injuries.

Statistical analyses were done on the different conditions (one way ANOVA followed by the Dunnett's or PLSD Fisher's test when it was allowed, Statview software version 5.0). $p<0.05$ was considered as significant.

2. Results 2.1. Results Obtained for Plant Extract NSP02-14-E001 (Ethanolic Extract of *Dioscorea persimilis*)

The results are given in FIG. 1.

Glutamate (40 μM, 20 min) induced a significant neuronal death (~30%). In presence of NSP02-14-E002 (500 ng/mL to 5 μg/mL) added 1 h before the glutamate and let during the toxic application and let for the next 48 h after wash-out, a significant protective effect was observed (~80% of survival) on the neuron survival (FIG. 1A) and neuritic network (FIG. 1B).

Plant extract NSP02-14-E001 was analyzed with using a DIONEX Acclaim® C18 column (2.2 μm, 150×2.1 mm) at 50° C., as mentioned above at point 1.1, in order to identify the potential neuroprotective compounds presents in the extract. The results are given in FIG. 10.

Plant extract NSP02-14-E001 (*Dioscorea persimilis*) contained catechin and traces of diosgenin derivative (dioscin).

2.2. Results Obtained for Plant Extract NSP02-29-E001 (Aqueous Extract of *Dioscorea villosa*)

Figure 2:
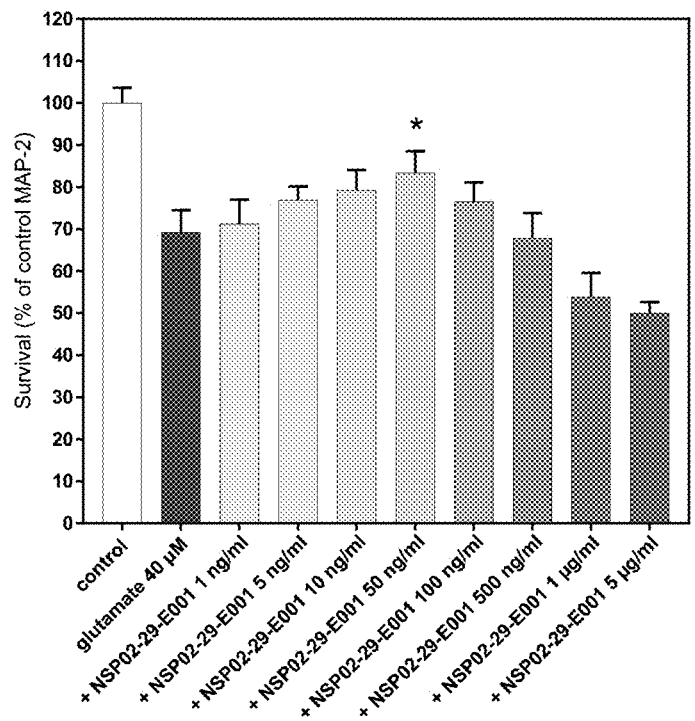
FIGS. 2A and 2B illustrate the effect of Glutamate (40 µM, 20 min) in presence or absence of NSP02-29-E001 (different concentrations) on primary cortical neuron survival (FIG. 2A) and neurite network (FIG. 2B). Data were expressed as percentage of control as mean±SEM (100%=no glutamate). *$p<0.05$ vs glutamate (one way ANOVA followed by PLSD Fisher test).
FIG. 2C shows concentration of different compounds in dose of extract tested—NSP02-29-E001 (in grey, the range of active concentrations).

The results are given in FIG. 2.

Figure 2B:
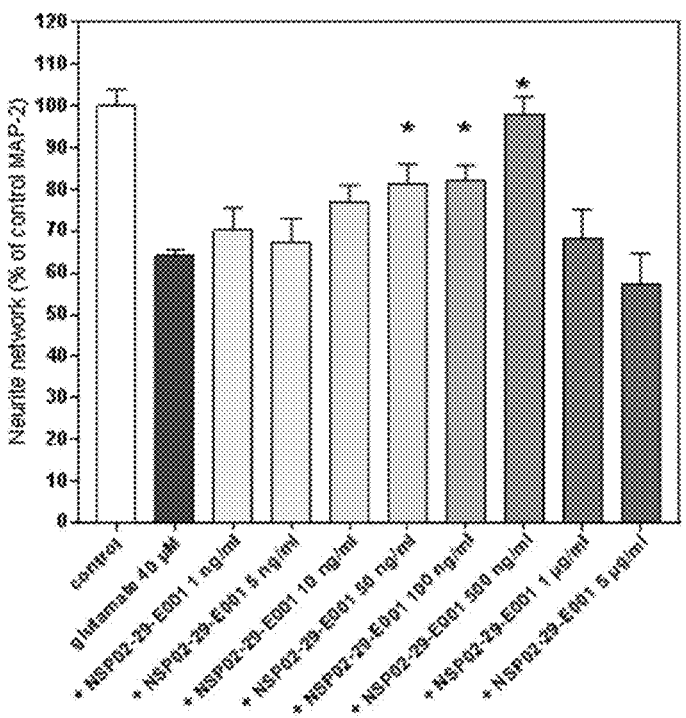

Glutamate (40 μM, 20 min) induced a significant neuronal death (~30%). In presence of NSP02-29-E001 (10-500 ng/ml) added 1 h before the glutamate and let during the toxic application and let for the next 48 h after wash-out, a protective effect was observed (~80% of survival) on the neuron survival (FIG. 2A) and neuritic network (FIG. 2B) which a significant protective effect between 50 and 500 ng/mL.

At the highest concentrations of extract were toxic

Plant extract NSP02-29-E001 was analyzed with using a DIONEX Acclaim® C18 column (2.2 μm, 150×2.1 mm) at 50° C., as mentioned above at point 1.1, in order to identify the potential neuroprotective compounds presents in the extract. The results are given in FIG. 2C.

Plant extract NSP02-29-E001 (*Dioscorea villosa*) contained catechin and diosgenin derivatives (dioscin and protodioscin).

2.3. Results Obtained for Plant Extract NSP02-29-E002 (Hydroalcoolic Extract of *Dioscorea villosa*)

Figure 3:
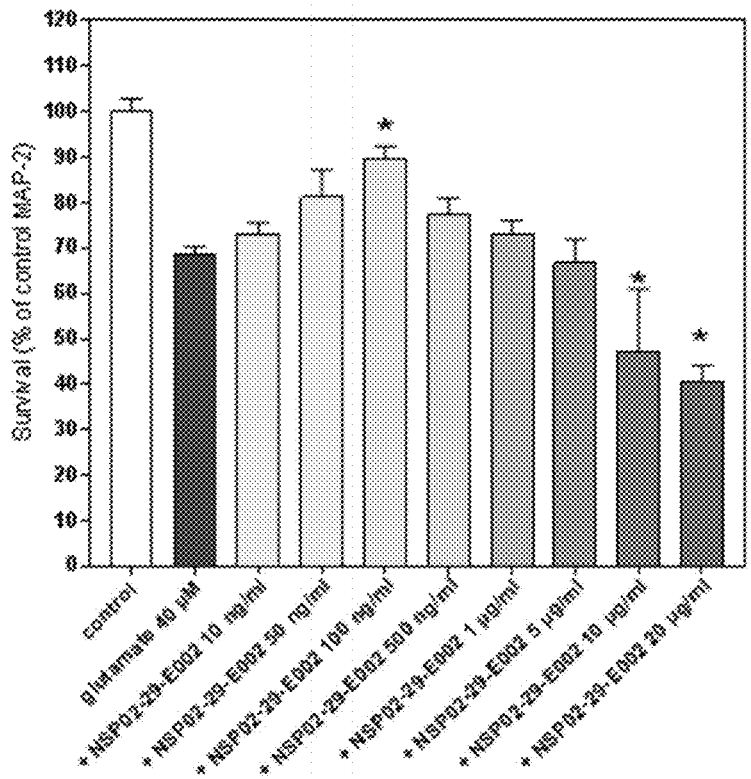
FIG. 3A and FIG. 3B illustrate the effect of Glutamate (40 µM, 20 min) in presence or absence of NSP02-29-E002 (different concentrations) on primary cortical neuron survival (FIG. 3A) and neurite network (FIG. 3B). Data were expressed as percentage of control as mean±SEM (100%=no glutamate). *$p<0.05$ vs glutamate (one way ANOVA followed by PLSD Fisher test).
FIG. 3C shows concentration of different compounds in dose of extract tested—NSP02-29-E002 (in grey, the range of active concentrations).
Figure 3:
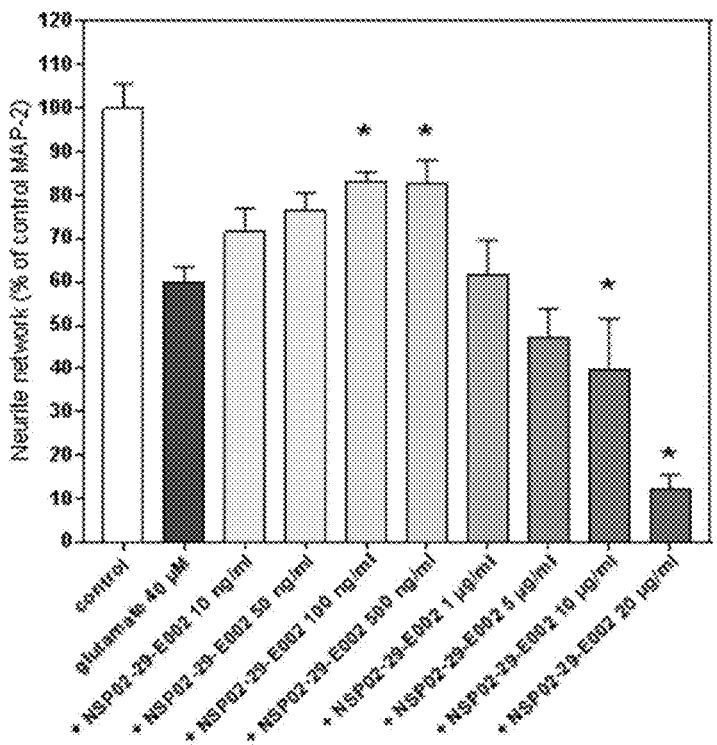

The results are given in FIG. 3.

Glutamate (40 μM, 20 min) induced a significant neuronal death (~30%). In presence of NSP02-29-E002 (50-500 ng/ml) added 1 h before the glutamate and let during the toxic application and let for the next 48 h after wash-out, a protective effect was observed (~80% of survival) on the neuron survival (FIG. 3A) and neuritic network (FIG. 3B) which a significant protective effect between 100 and 500 ng/mL.

At the highest concentrations of extract were toxic.

Plant extract NSP02-29-E002 was analyzed with using a DIONEX Acclaim® C18 column (2.2 μm, 150×2.1 mm) at 50° C., as mentioned above at point 1.1, in order to identify the potential neuroprotective compounds presents in the extract. The results are given in FIG. 3C.

Plant extract NSP02-29-E002 (*Dioscorea villosa*) contained catechin and traces of diosgenin derivative (dioscin and protodioscin).

2.4. Results Obtained for Plant Extract NSP19-30-E002 (Hydroalcoolic Extract of *Asparagus officinalis*)

The results are given in FIG. 4.

Figure 4A:
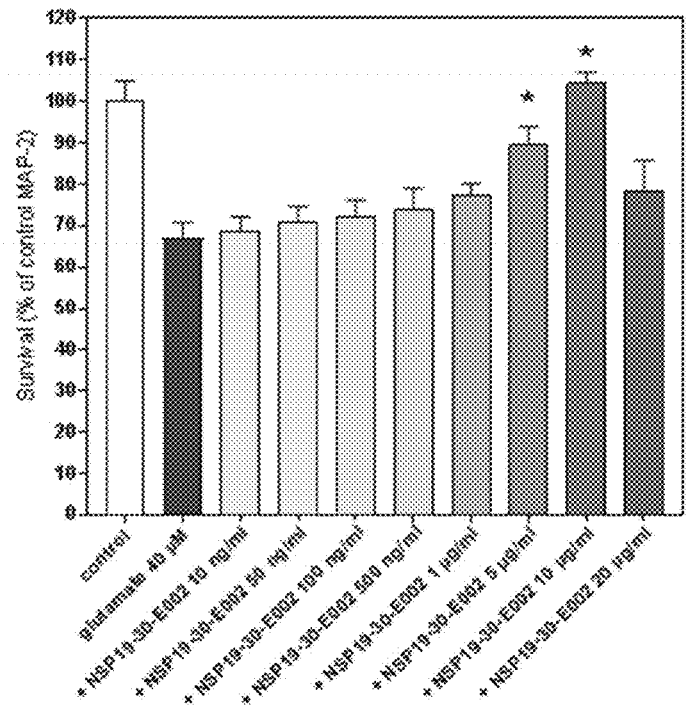
FIG. 4A and FIG. 4B illustrate the effect of Glutamate (40 µM, 20 min) in presence or absence of NSP19-30-E002 (different concentrations) on primary cortical neuron survival (FIG. 4A) and neurite network (FIG. 4B). Data were expressed as percentage of control as mean±SEM (100%=no glutamate). *$p<0.05$ vs glutamate (one way ANOVA followed by PLSD Fisher test).
Figure 4B:
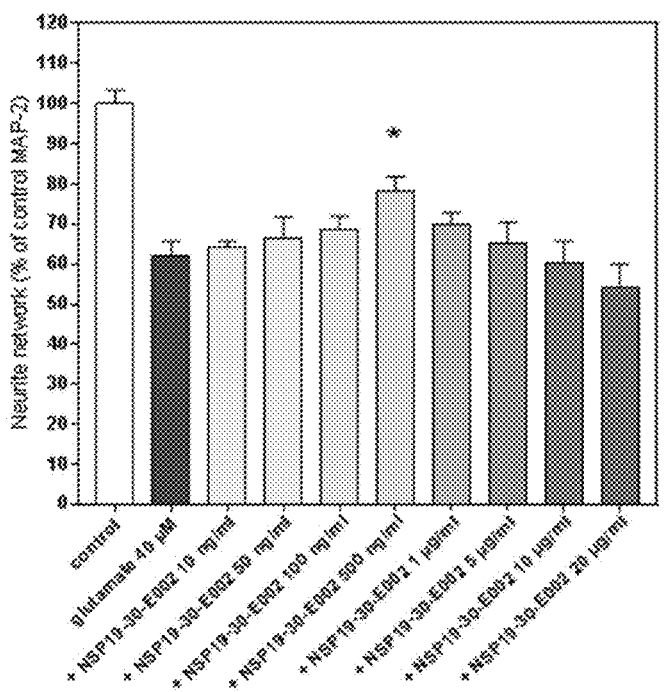

Glutamate (40 μM, 20 min) induced a significant neuronal death (~30%). In presence of NSP19-30-E002 (500 ng/mL-10 μg/ml) added 1 h before the glutamate and let during the toxic application and let for the next 48 h after wash-out, a significant protective effect was observed (~80% of survival) on the neuron survival (FIG. 4A) and/or neuritic network (FIG. 4B).

Plant extract NSP19-30-E002 was analyzed with using a DIONEX Acclaim® C18 column (2.2 μm, 150×2.1 mm) at 50° C., as mentioned above at point 1.1, in order to identify the potential neuroprotective compounds presents in the extract. The results are given in FIG. 4C.

Plant extract NSP19-30-E002 (*Asparagus officinalis*) contained sarsasapogenin, caffeic acid and coumaric acid.

2.5. Results Obtained for Plant Extract NSP20-31-E002 (Hydroalcoolic Extract of *Smilax aspera*)

The results are given in FIG. 5.

Figure 5A:
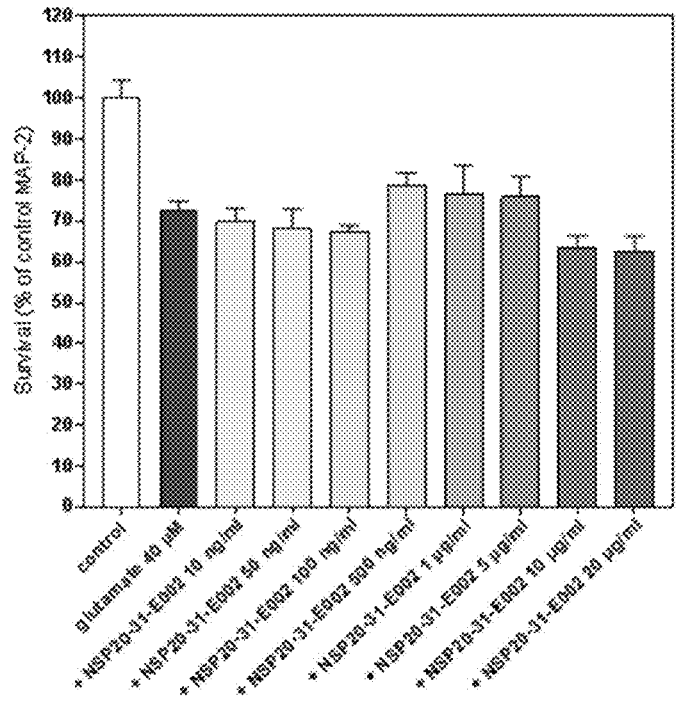
FIG. 5A and FIG. 5B illustrate the effect of Glutamate (40 µM, 20 min) in presence or absence of NSP20-31-E002 (different concentrations) on primary cortical neuron survival (FIG. 5A) and neurite network (FIG. 5B). Data were expressed as percentage of control as mean±SEM (100%=no glutamate). *$p<0.05$ vs glutamate (one way ANOVA followed by PLSD Fisher test).
Figure 5B:
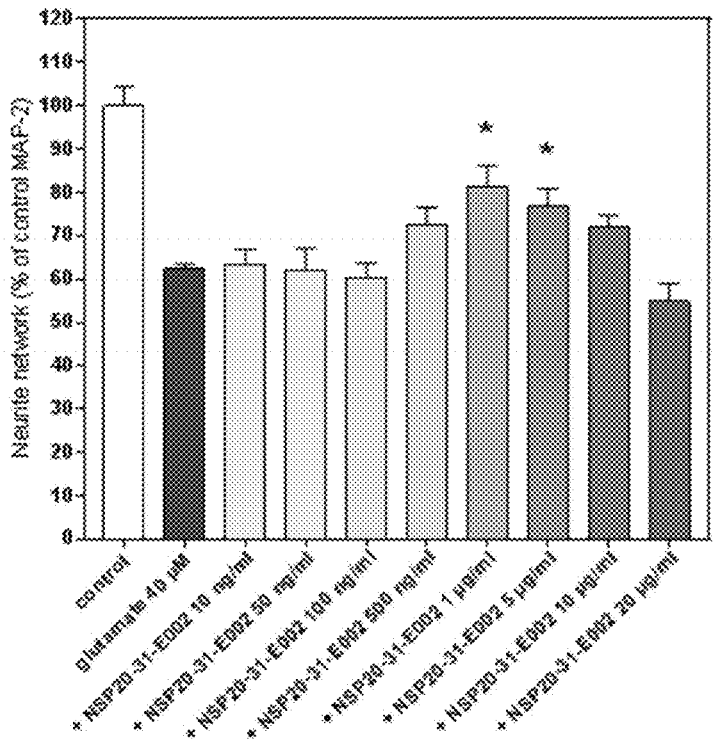

Glutamate (40 μM, 20 min) induced a significant neuronal death (~30%) (FIG. 5A). In presence of NSP19-30-E002 (1 μg/mL-5 μg/ml) added 1 h before the glutamate and let during the toxic application and let for the next 48 h after wash-out, a significant protective effect was observed (~80% of survival) on the neuritic network (FIG. 5B).

Plant extract NSP19-30-E002 was analyzed with using a DIONEX Acclaim® C18 column (2.2 μm, 150×2.1 mm) at 50° C., as mentioned above at point 1.1, in order to identify the potential neuroprotective compounds presents in the extract. The results are given in FIG. 5C.

Plant extract NSP19-30-E002 (*Smilax aspera*) contained sarsasapogenin.

Example 2

Evaluation of the Neuroprotective Effect of Sarsasapogenin (SAR), Diosgenin (DIOSG), Dioscin (DIOS), Quercetin, Catechin, Caffeic Acid (CAF), Coumaric Acid (COU), Ferulic Acid (FA) and Qallic Acid An acute analytical analysis of the chemical profile of NSP02-29-E001, NSP02-29-E002 and NSP19-30-E002 extract was done. Several compounds were suspected to be involved in this effect and to act synergically. In this study, the neuroprotective effect of a mixture of single molecules on primary cortical neurons injured by glutamate exposure was assessed according to the method given in example 1.

1. Effect of Sarsasapogenin (SAR, Steroidal Saponin).

The results are given in FIG. 6.

Figure 6A:
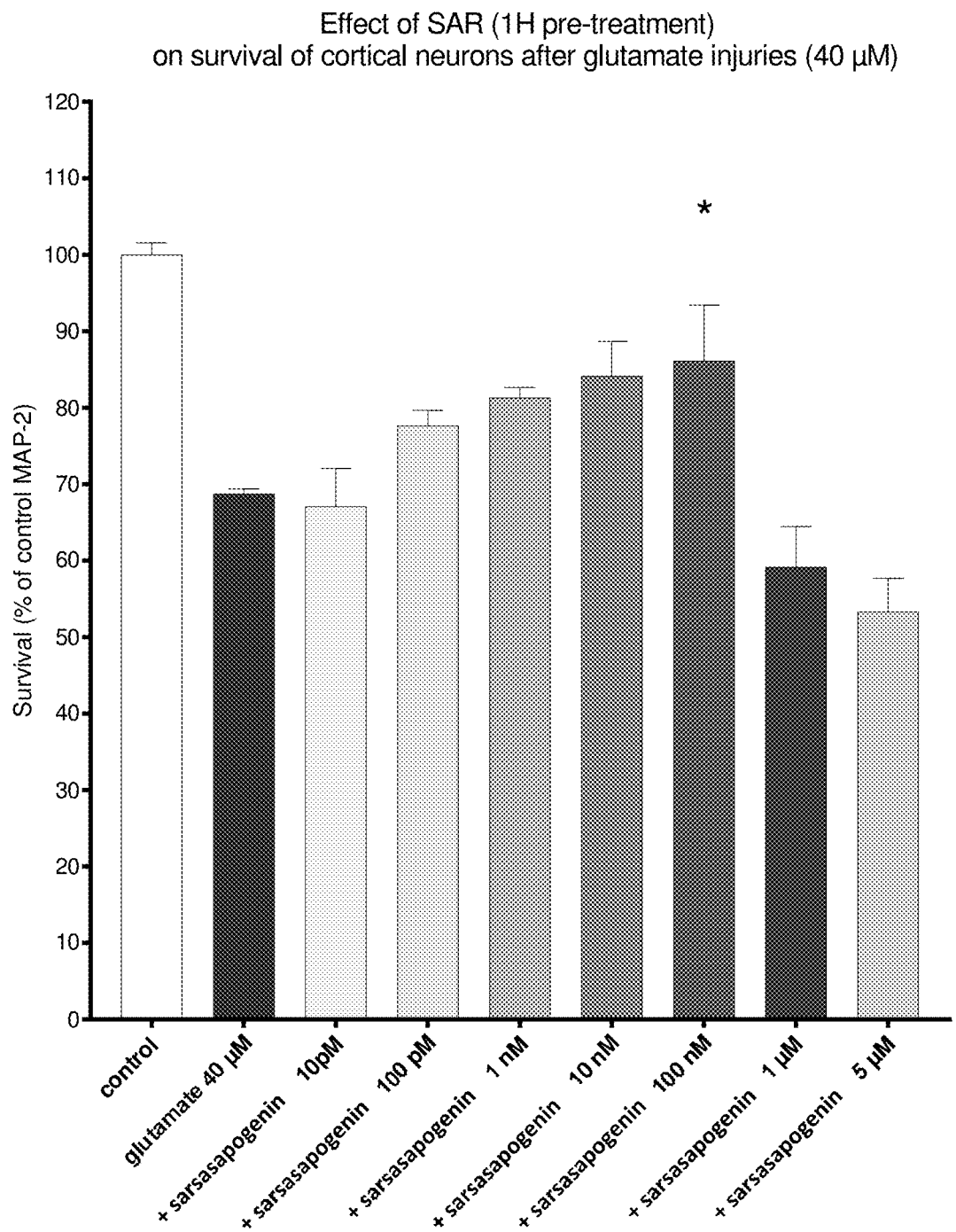
FIG. 6A and FIG. 6B illustrate the effect of Glutamate (40 µM, 20 min) in presence or absence of sarsasapogenin (SAR) (different concentrations) on primary cortical neuron survival (FIG. 6A) and neurite network (FIG. 6B). Data were expressed as percentage of control as mean±SEM (100%=no glutamate). *$p<0.05$ vs glutamate (one way ANOVA followed by Dunnett's test).
Figure 6B:
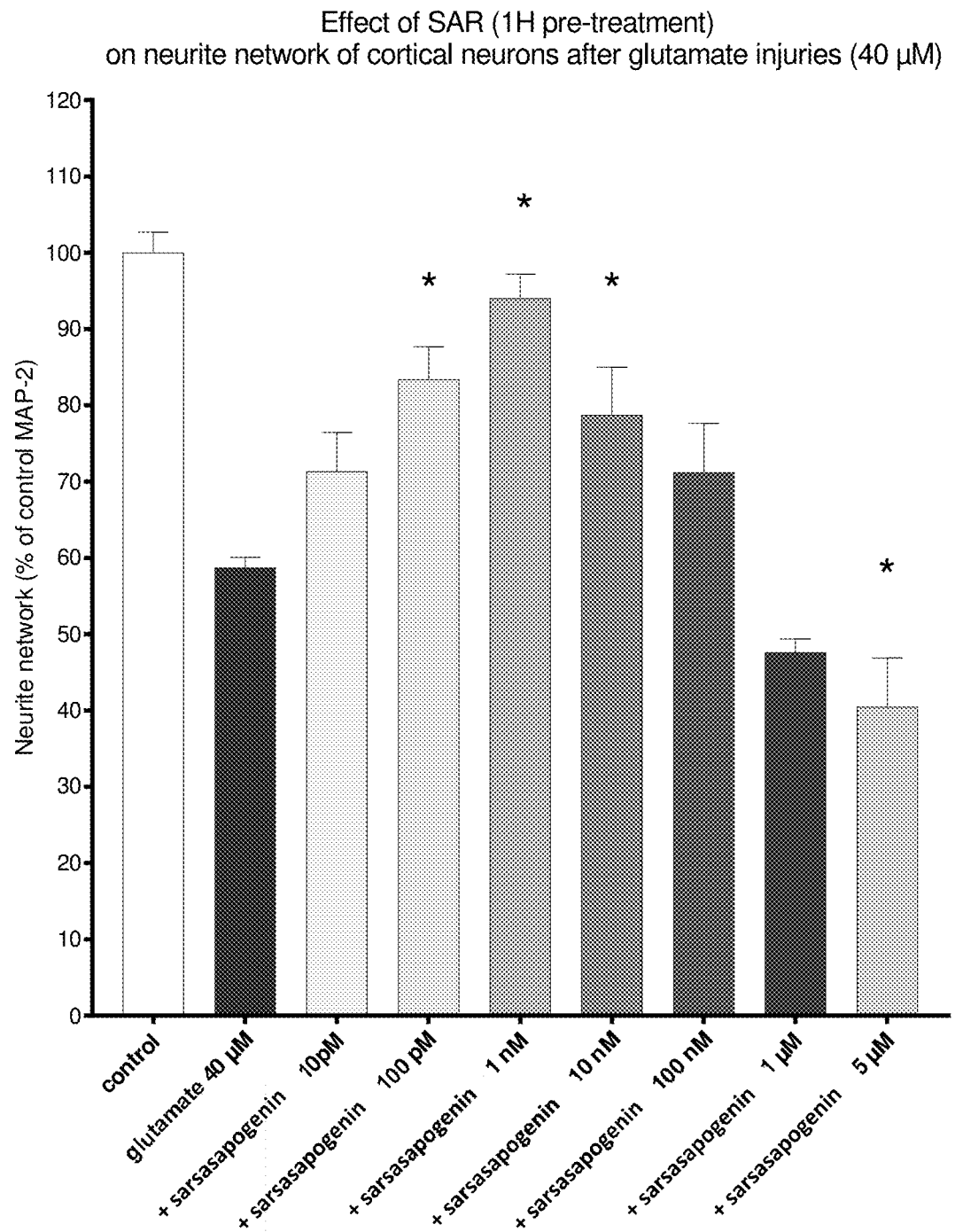

Glutamate (40 µM, 20 min) induced a significant neuronal death (~30%). In presence of SAR (100 pM-100 nM) added 1 h before the glutamate and let during the toxic application and let for the next 48 h after wash-out, a protective effect was observed (~80% of survival) on the neuron survival and neuritic network which a significant protective effect between 100 pM and 10 nM for neuritic network (FIG. 6B) and 100 nM for neuron survival (FIG. 6A).

At the highest concentrations of extract were toxic.

2. Effect of Diosgenin (DIOSG, Steroidal Saponin).

The results are given in FIG. 7.

Figure 7A:
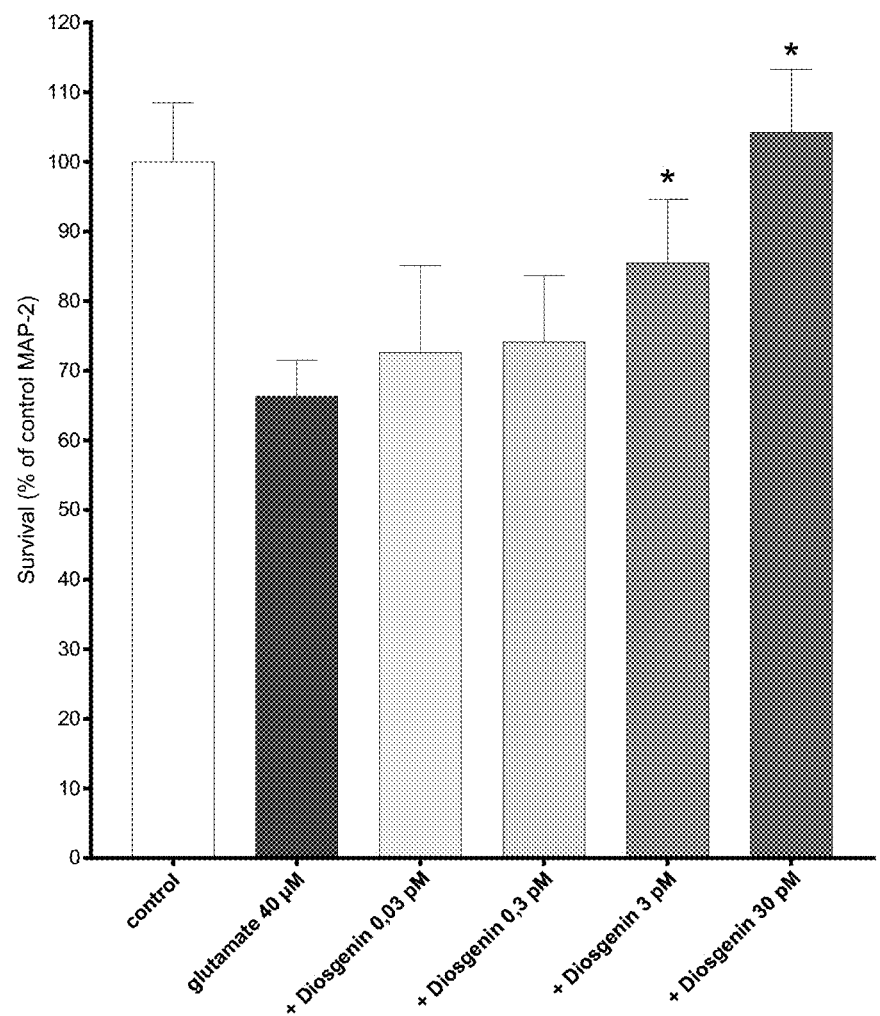
FIG. 7A and FIG. 7B illustrate the effect of Glutamate (40 µM, 20 min) in presence or absence of diosgenin (different concentrations) on primary cortical neuron survival (FIG. 7A) and neurite network (FIG. 7B). Data were expressed as percentage of control as mean±SEM (100%=no glutamate). *$p<0.05$ vs glutamate (one way ANOVA followed by Dunnett's test).
Figure 7B:
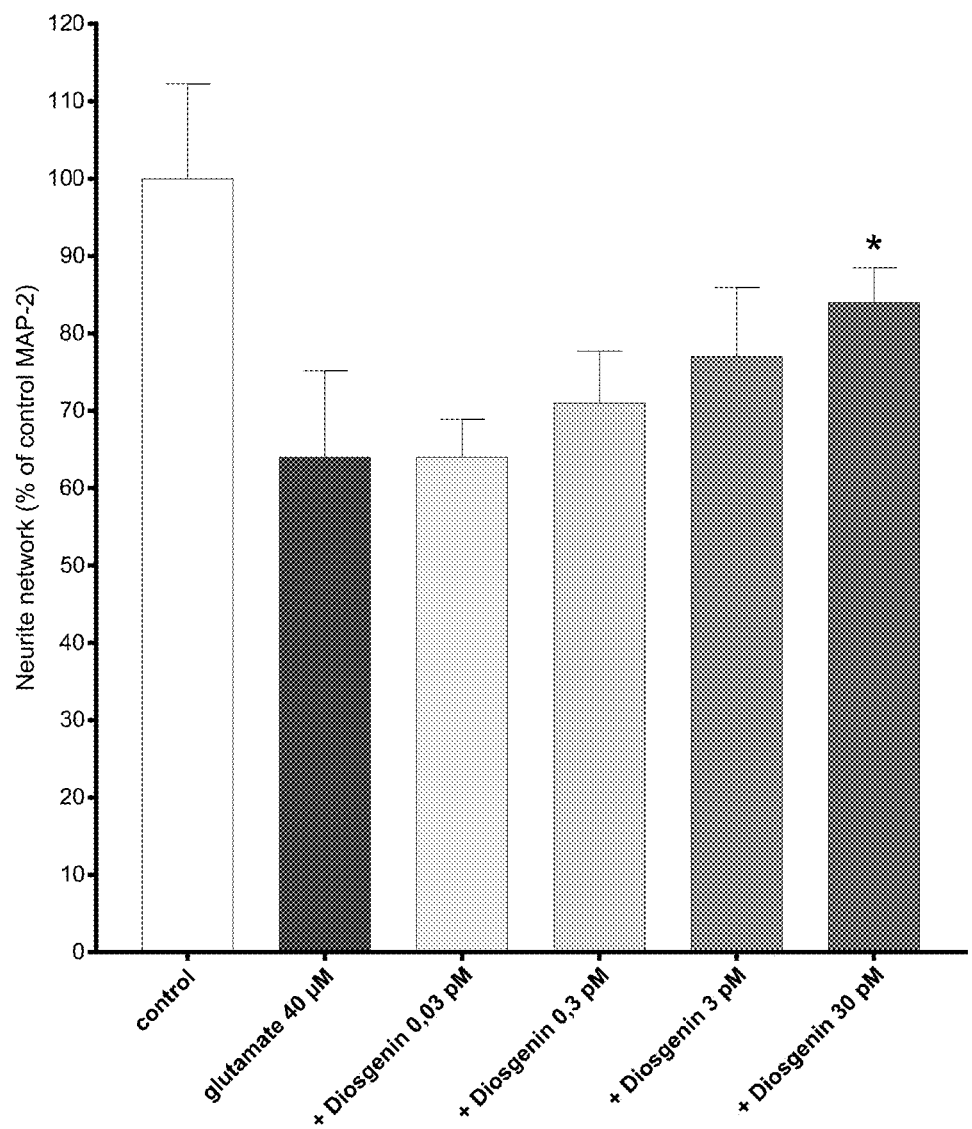

Glutamate (40 µM, 20 min) induced a significant neuronal death (~30%). In presence of DIOSG (3 pM-30 pM) added 1 h before the glutamate and let during the toxic application and let for the next 48 h after wash-out, a significant protective effect was observed (~80% of survival) on the neuron survival (FIG. 7A) and neuritic network (FIG. 7B).

3. Effect of Dioscin (DIO, Steroidal Saponin, Heterosidic Derivative of Diosgenin).

The results are given in FIG. 8.

Figure 8A:
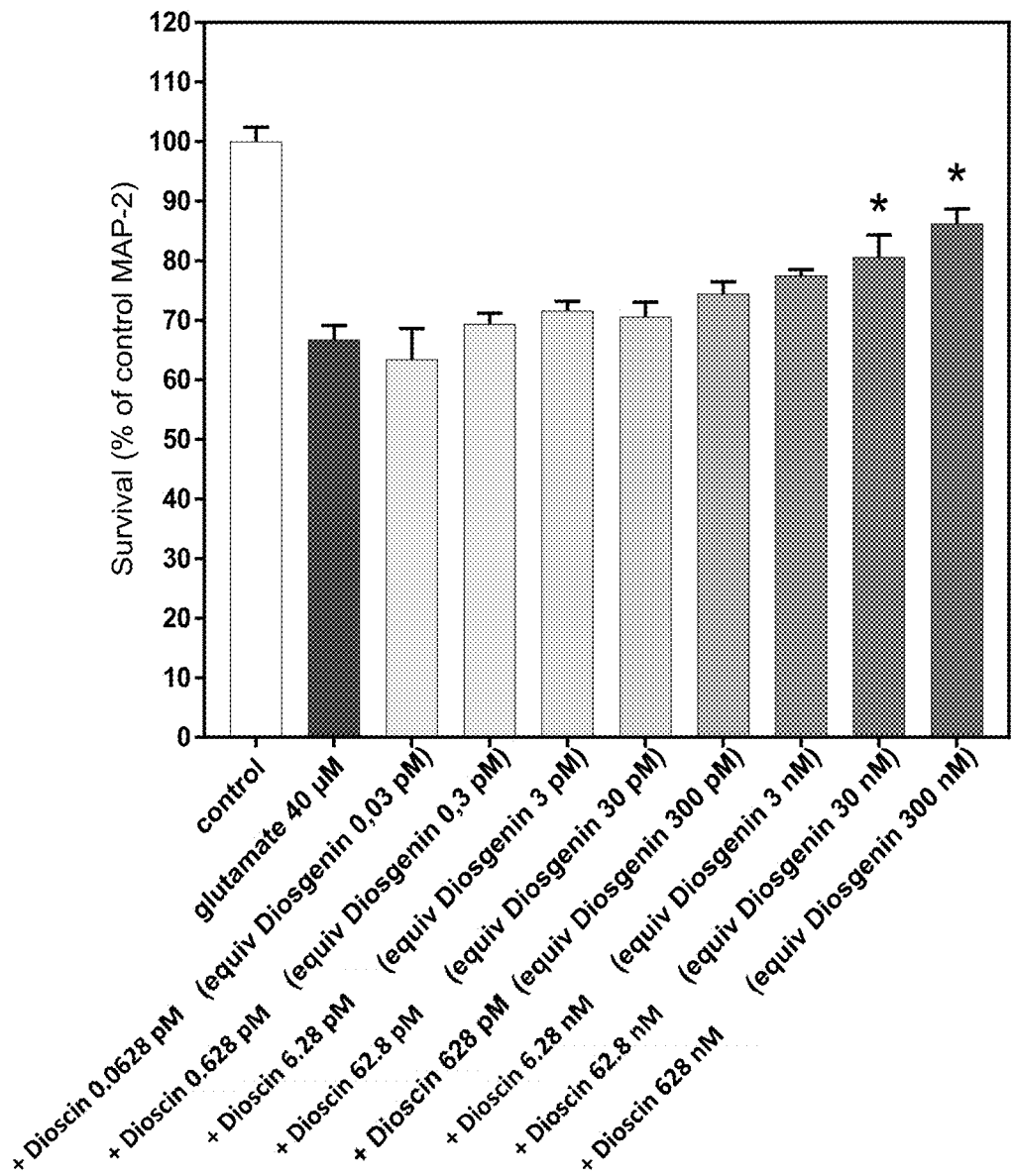
FIG. 8A and FIG. 8B illustrate the effect of Glutamate (40 µM, 20 min) in presence or absence of dioscin (different concentrations) on primary cortical neuron survival (FIG. 8A) and neurite network (FIG. 8B). Data were expressed as percentage of control as mean±SEM (100%=no glutamate). *$p<0.05$ vs glutamate (one way ANOVA followed by Dunnett's test).
Figure 8B:
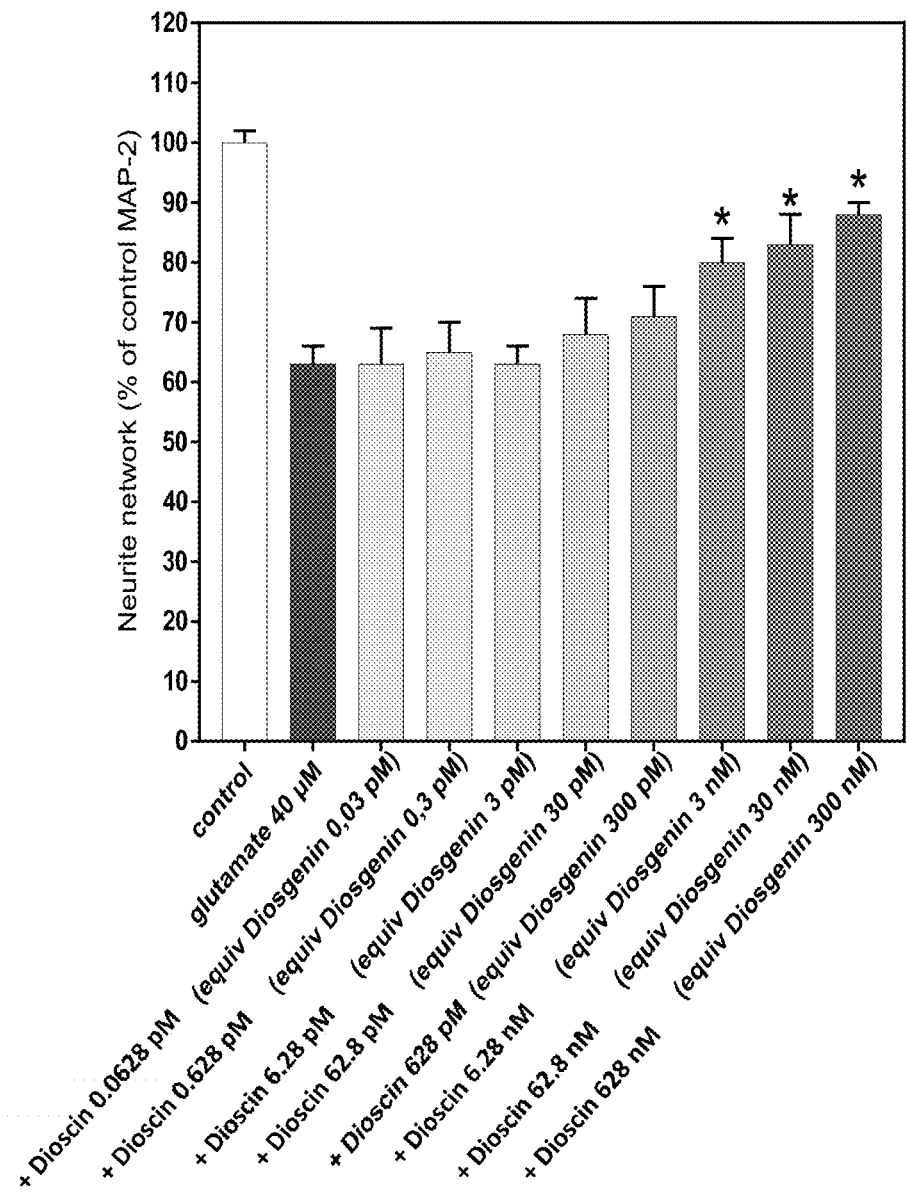
Figure 9A:
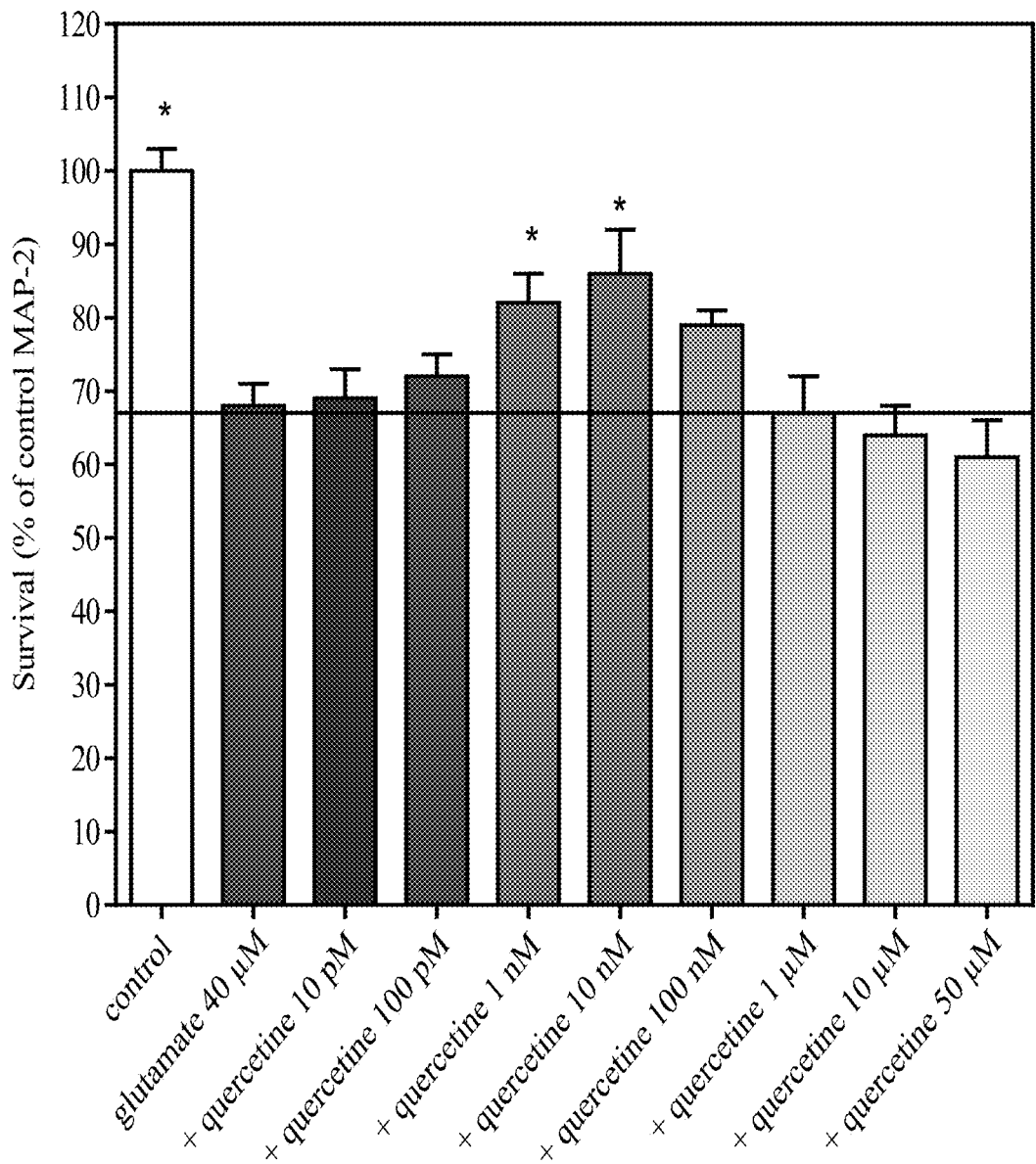
FIG. 9A and FIG. 9B illustrate the effect of Glutamate (40 µM, 20 min) in presence or absence of quercetin (different concentrations) on primary cortical neuron survival (FIG. 9A) and neurite network (FIG. 9B). Data were expressed as percentage of control as mean±SEM (100%=no glutamate). *$p<0.05$ vs glutamate (one way ANOVA followed by Dunnett's test).
Figure 9B:
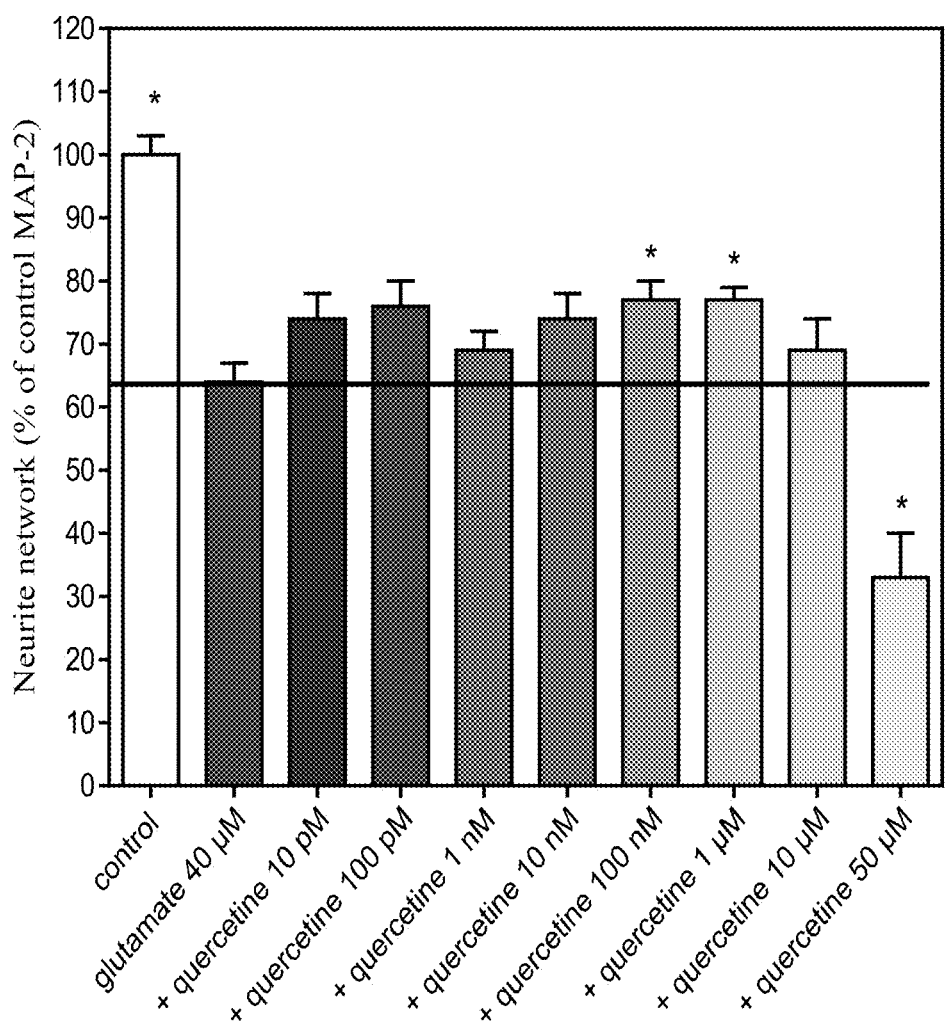
Figure 10A:
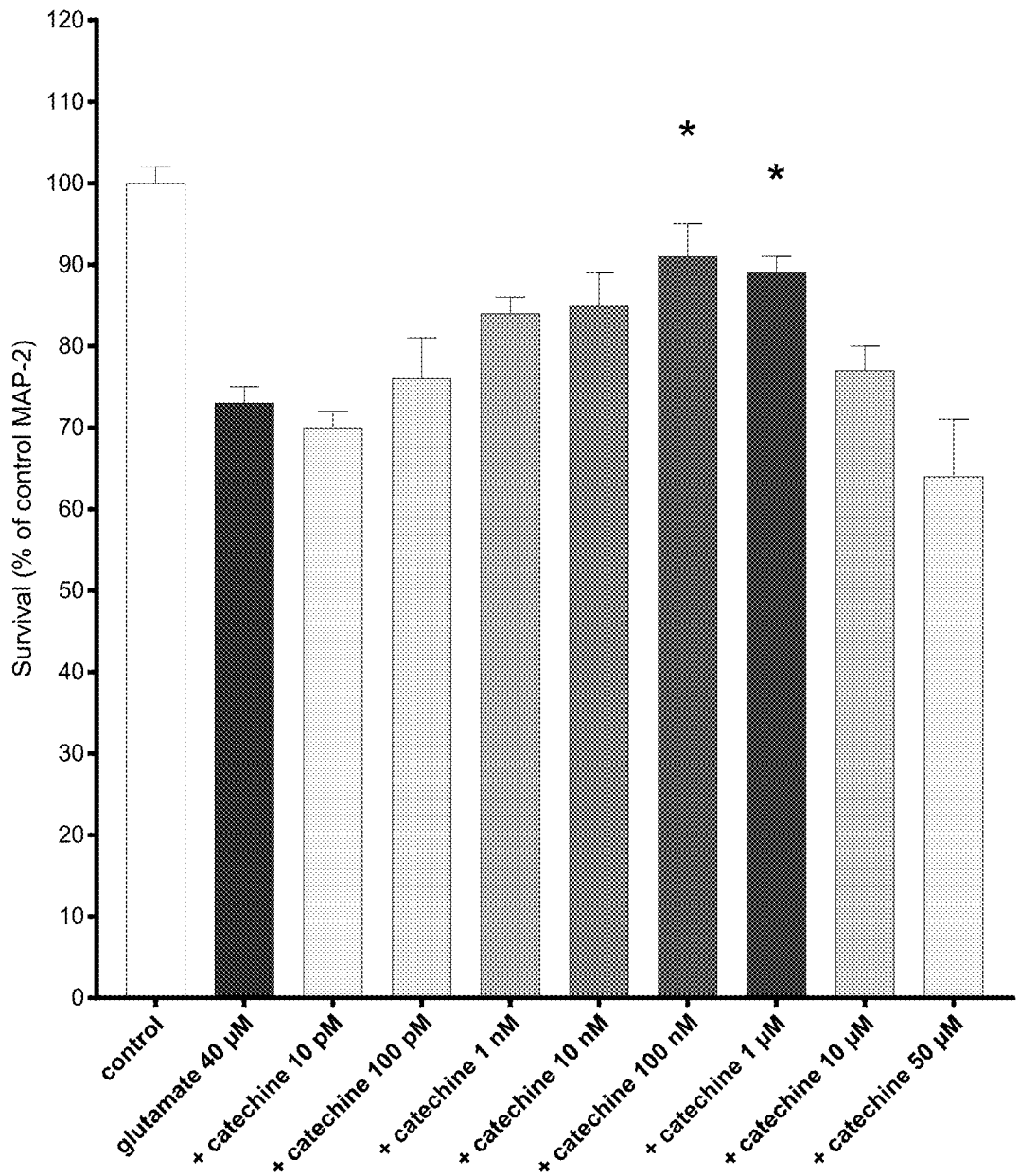
FIG. 10A and FIG. 10B illustrate the effect of Glutamate (40 µM, 20 min) in presence or absence of catechin (CAT) (different concentrations) on primary cortical neuron survival (FIG. 10A) and neurite network (FIG. 10B). Data were expressed as percentage of control as mean±SEM (100%=no glutamate). *p<0.05 vs glutamate (one way ANOVA followed by Dunnett's test).
Figure 10B:
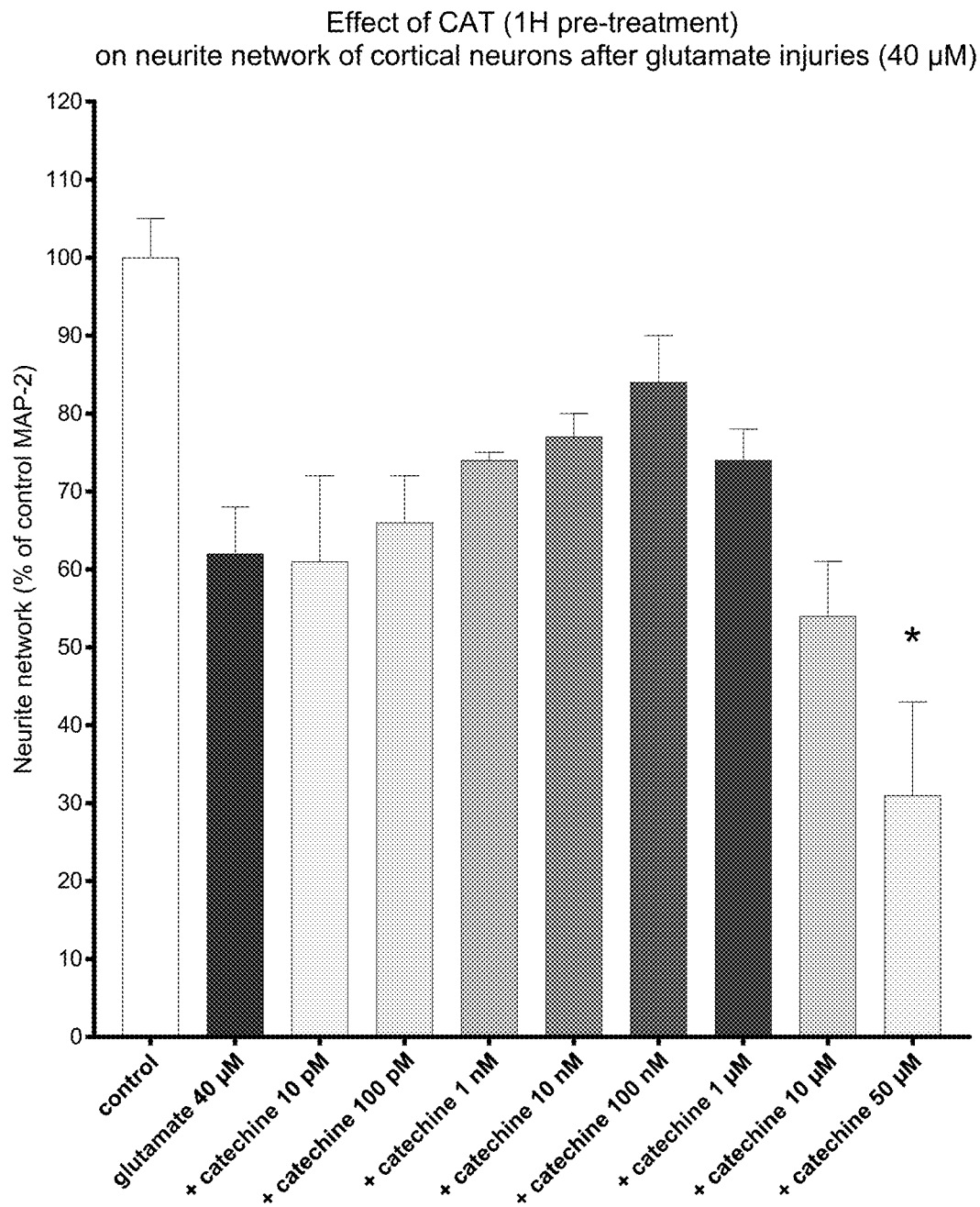
Figure 11A:
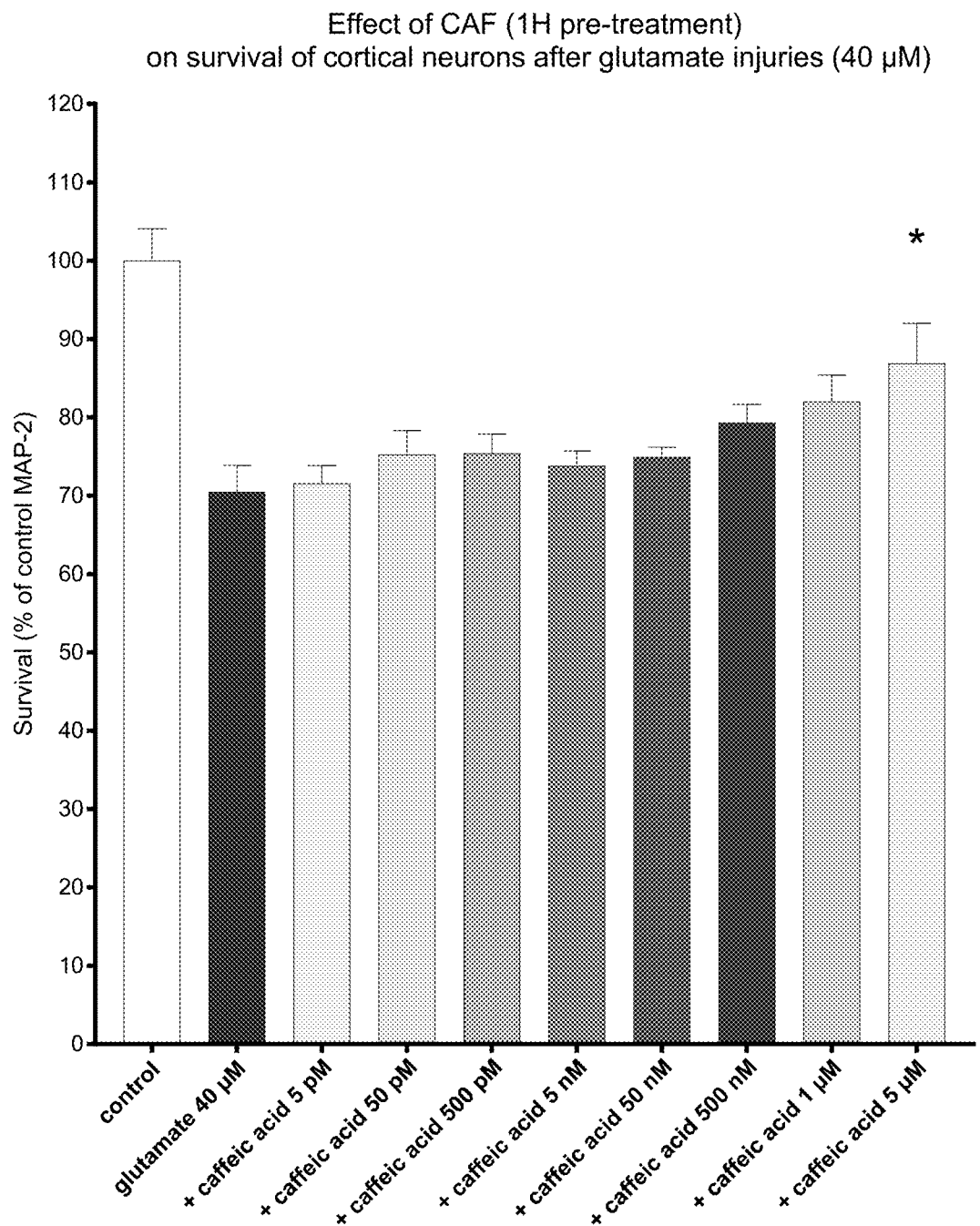
FIG. 11A and FIG. 11B illustrate the effect of Glutamate (40 µM, 20 min) in presence or absence of caffeic acid (CAF) (different concentrations) on primary cortical neuron survival (FIG. 11A) and neurite network (FIG. 11B). Data were expressed as percentage of control as mean±SEM (100%=no glutamate). *p<0.05 vs glutamate (one way ANOVA followed by Dunnett's test).
Figure 11B:
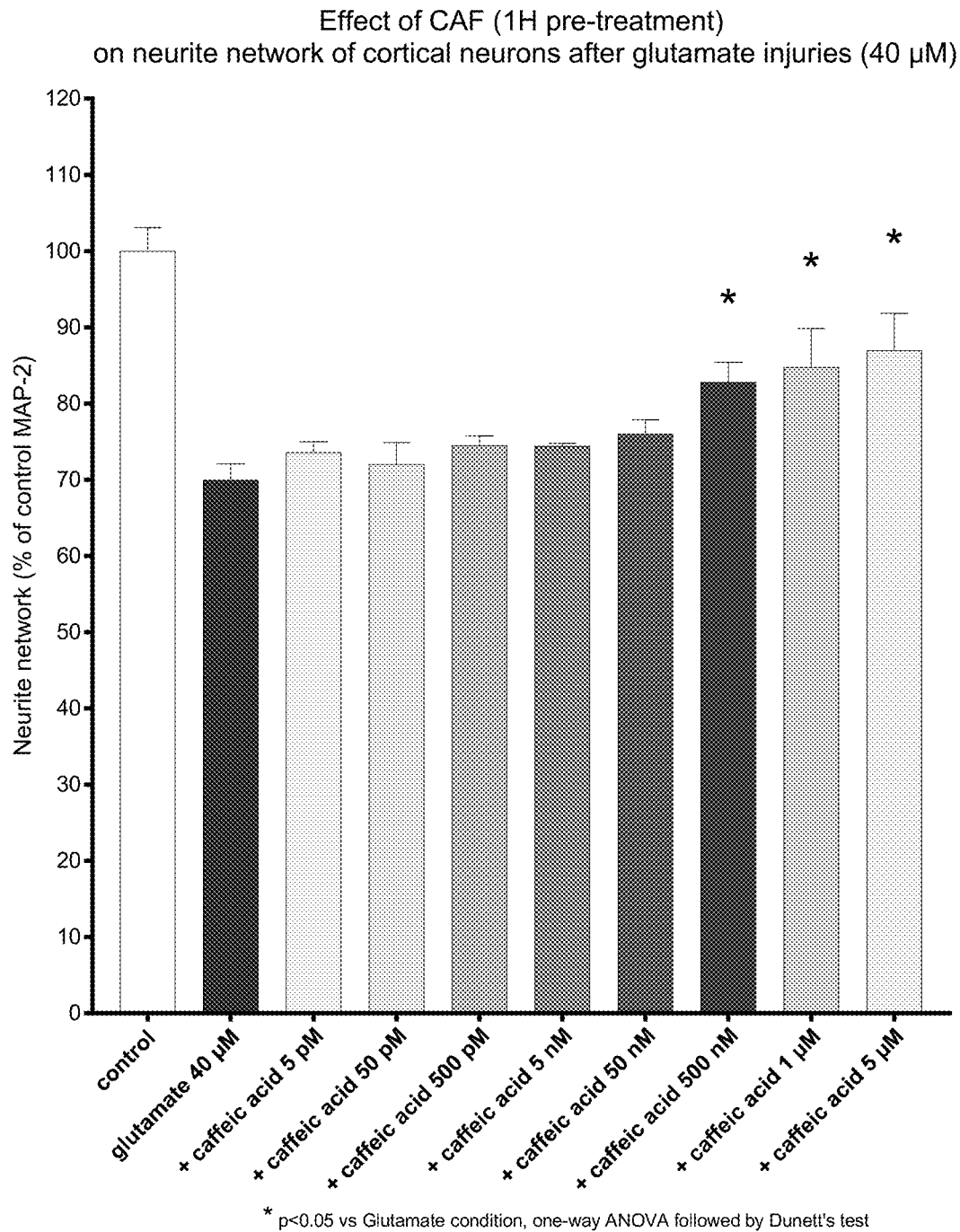
Figure 12A:
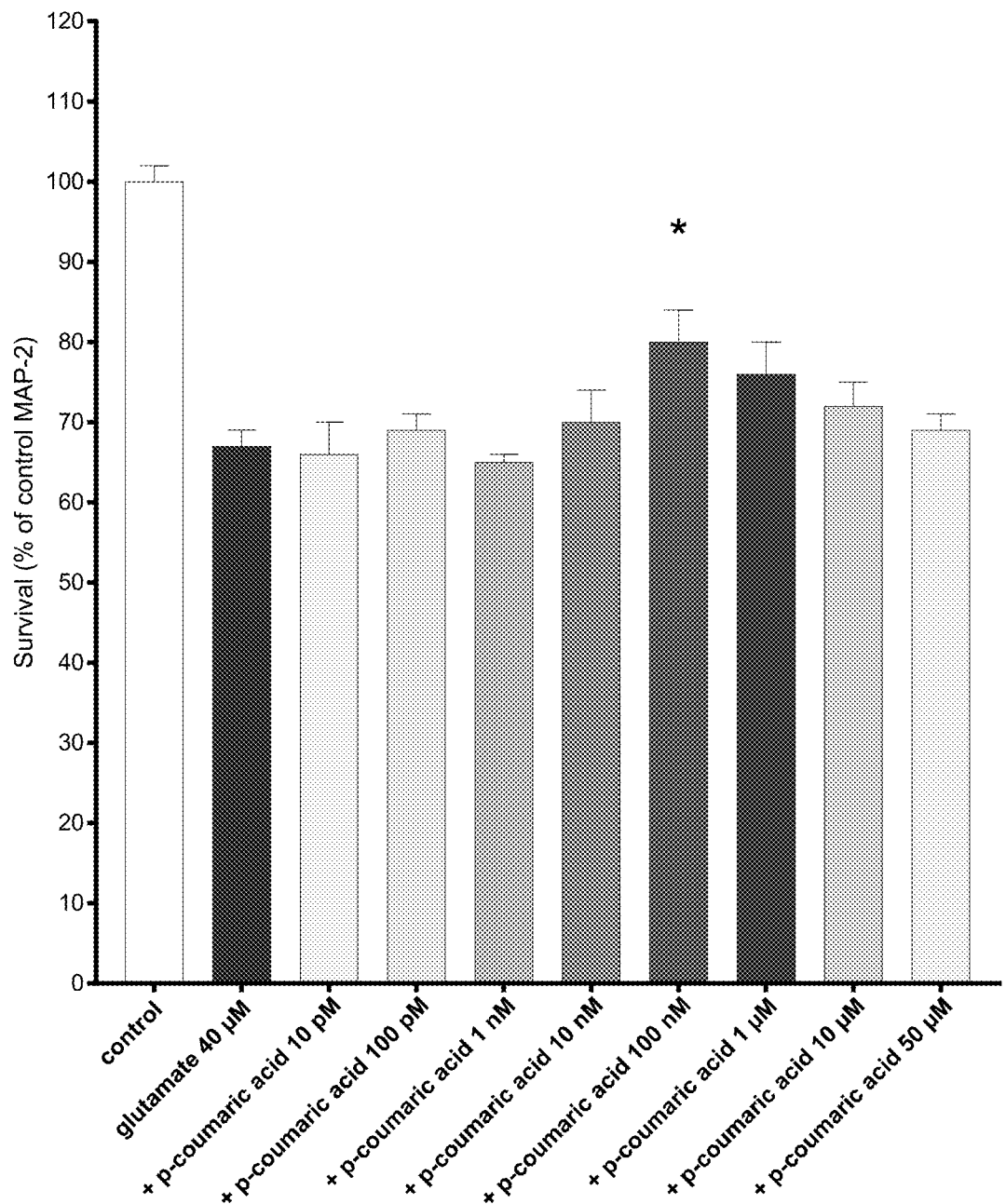
FIG. 12A and FIG. 12B illustrate the effect of Glutamate (40 µM, 20 min) in presence or absence of coumaric acid (COU) (different concentrations) on primary cortical neuron survival (FIG. 12A) and neurite network (FIG. 12B). Data were expressed as percentage of control as mean±SEM (100%=no glutamate). *p<0.05 vs glutamate (one way ANOVA followed by Dunnett's test).
Figure 12B:
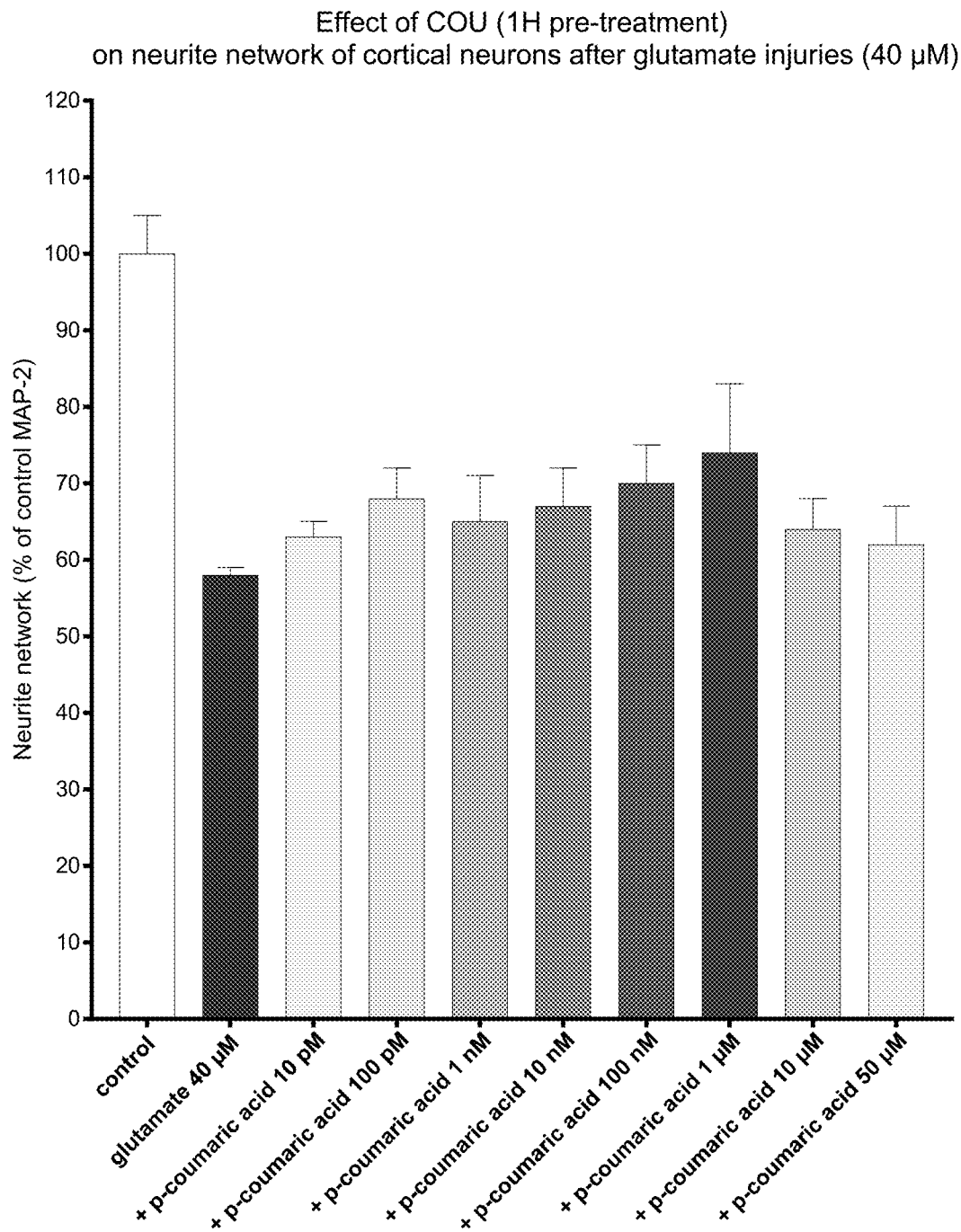
Figure 13A:
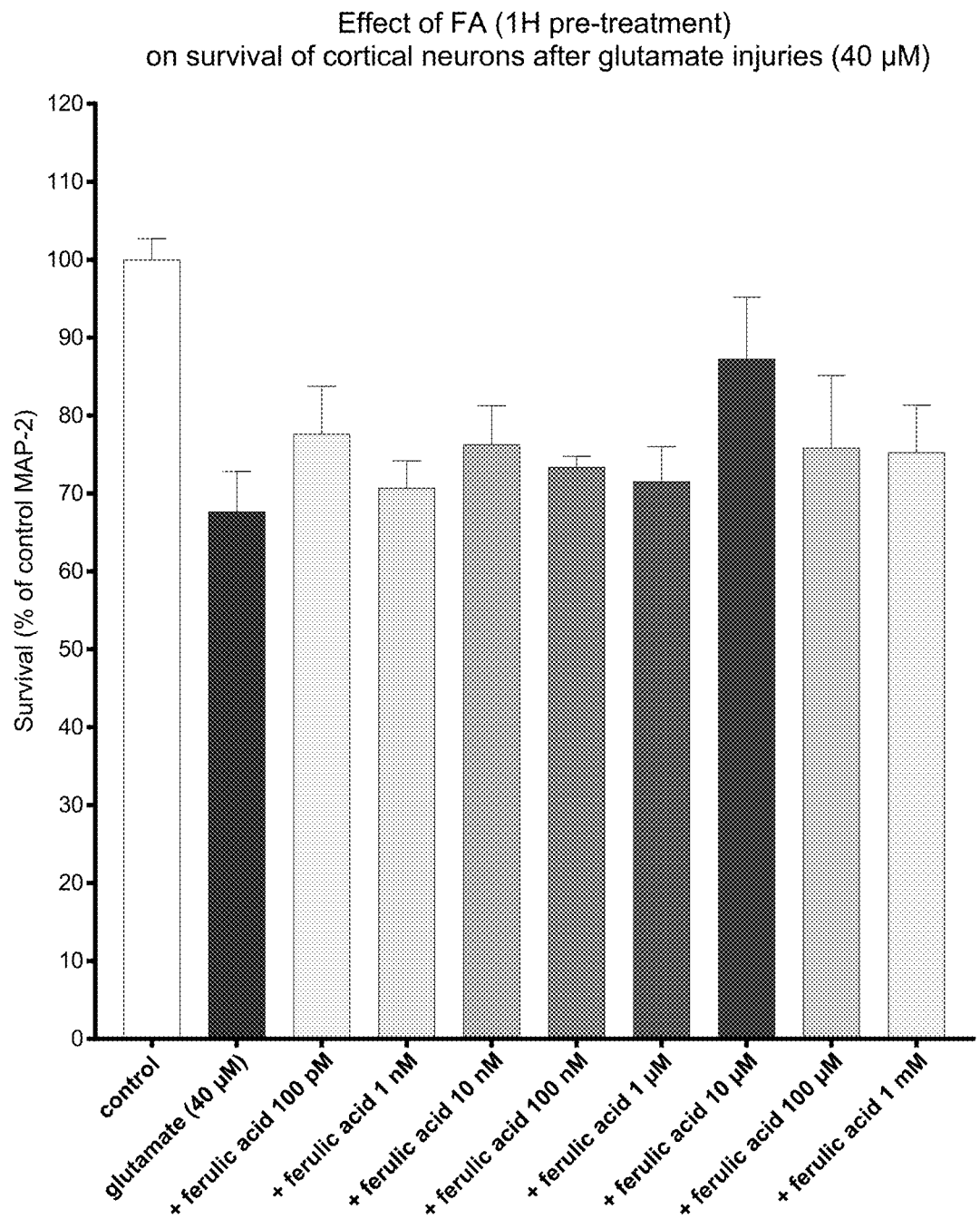
FIG. 13A and FIG. 13B illustrate the effect of Glutamate (40 µTA, 20 min) in presence or absence of ferulic acid (FA) (different concentrations) on primary cortical neuron survival (FIG. 13A) and neurite network (FIG. 13B). Data were expressed as percentage of control as mean±SEM (100%=no glutamate). *p<0.05 vs glutamate (one way ANOVA followed by Dunnett's test).
Figure 13B:
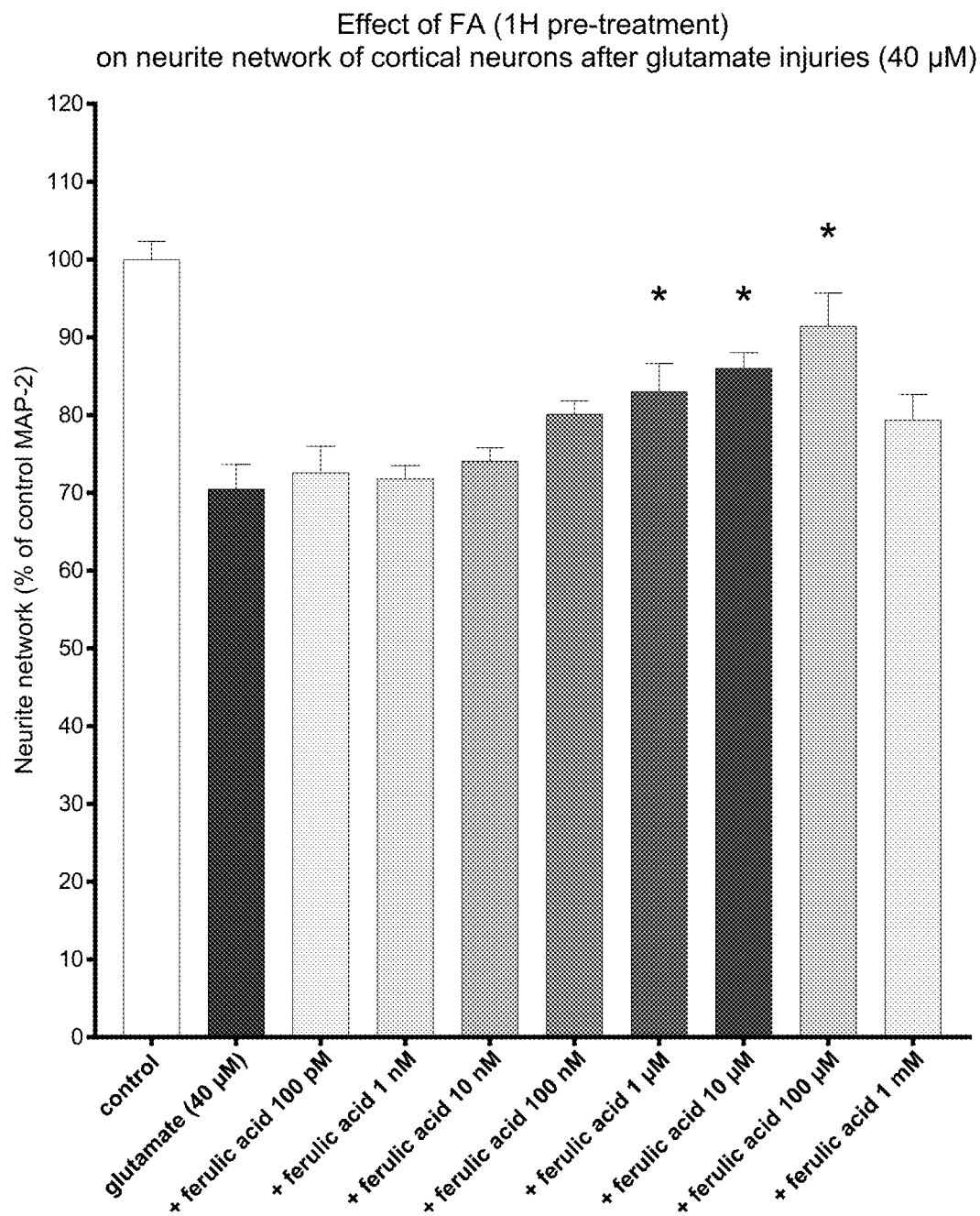
Figure 14A:
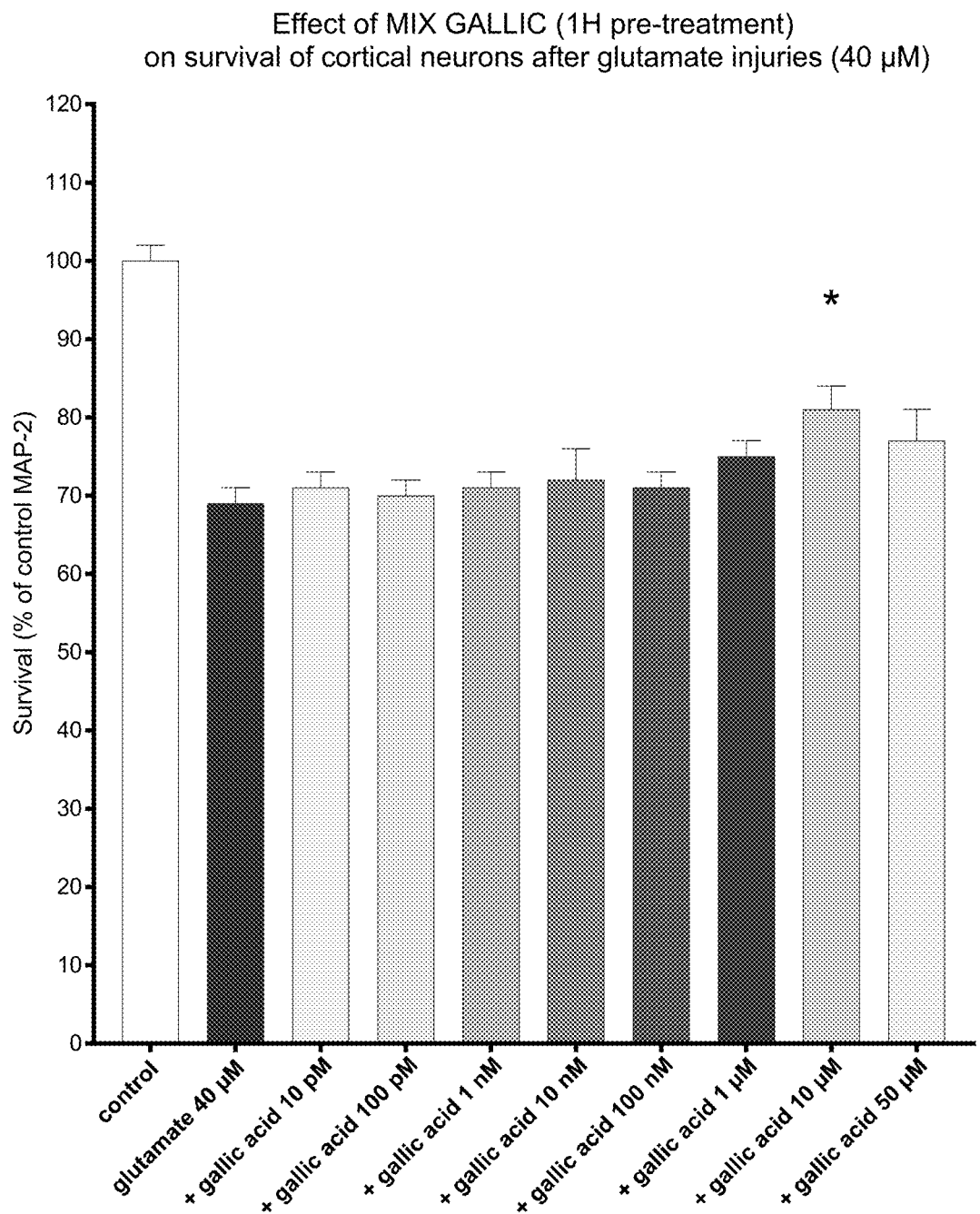
FIG. 14A and FIG. 14B illustrate the effect of Glutamate (40 µM, 20 min) in presence or absence of gallic acid (GALLIC) (different concentrations) on primary cortical neuron survival (FIG. 14A) and neurite network (FIG. 14B). Data were expressed as percentage of control as mean±SEM (100%=no glutamate).*p<0.05 vs glutamate (one way ANOVA followed by Dunnett's test).
Figure 14B:
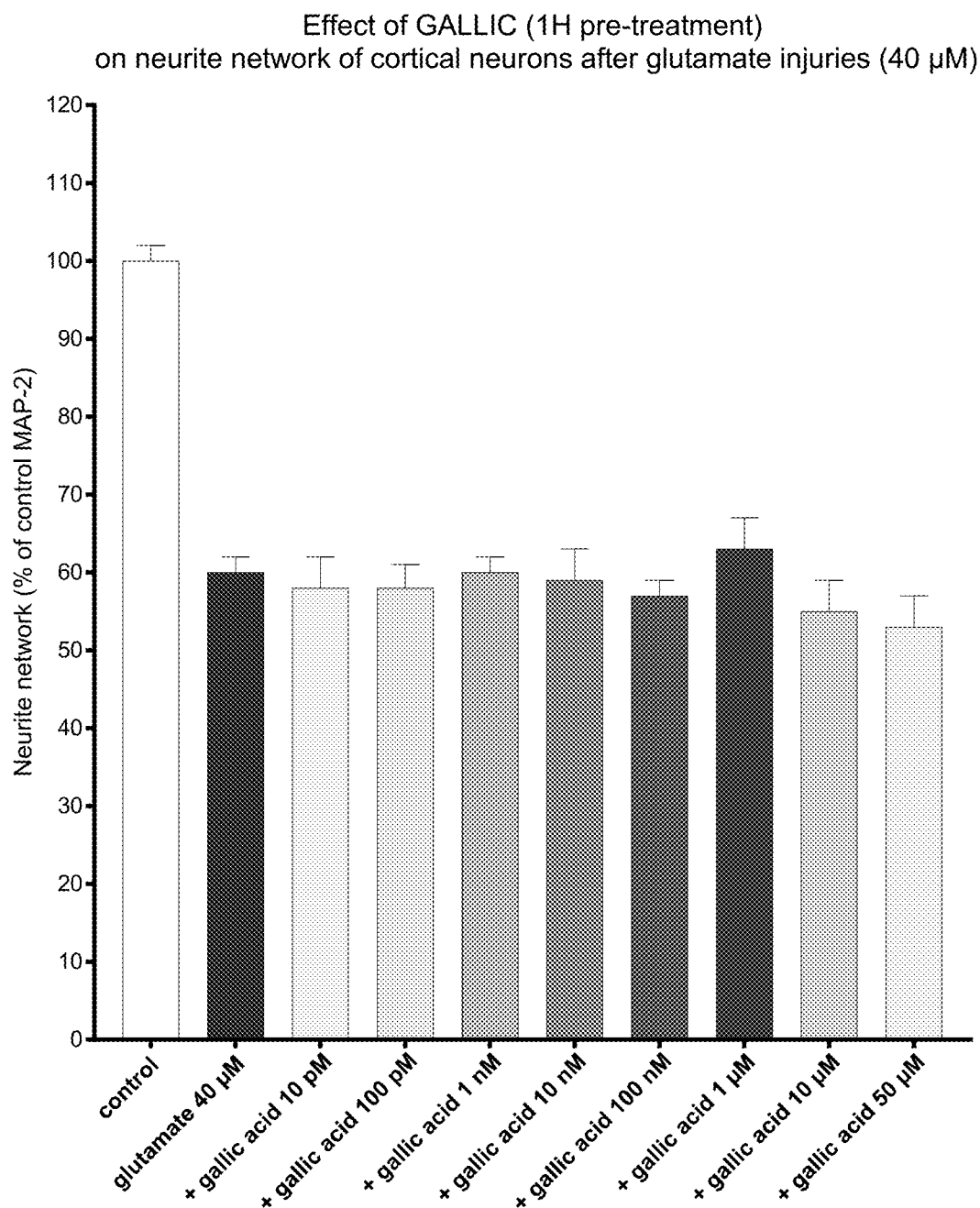
Figure 15:
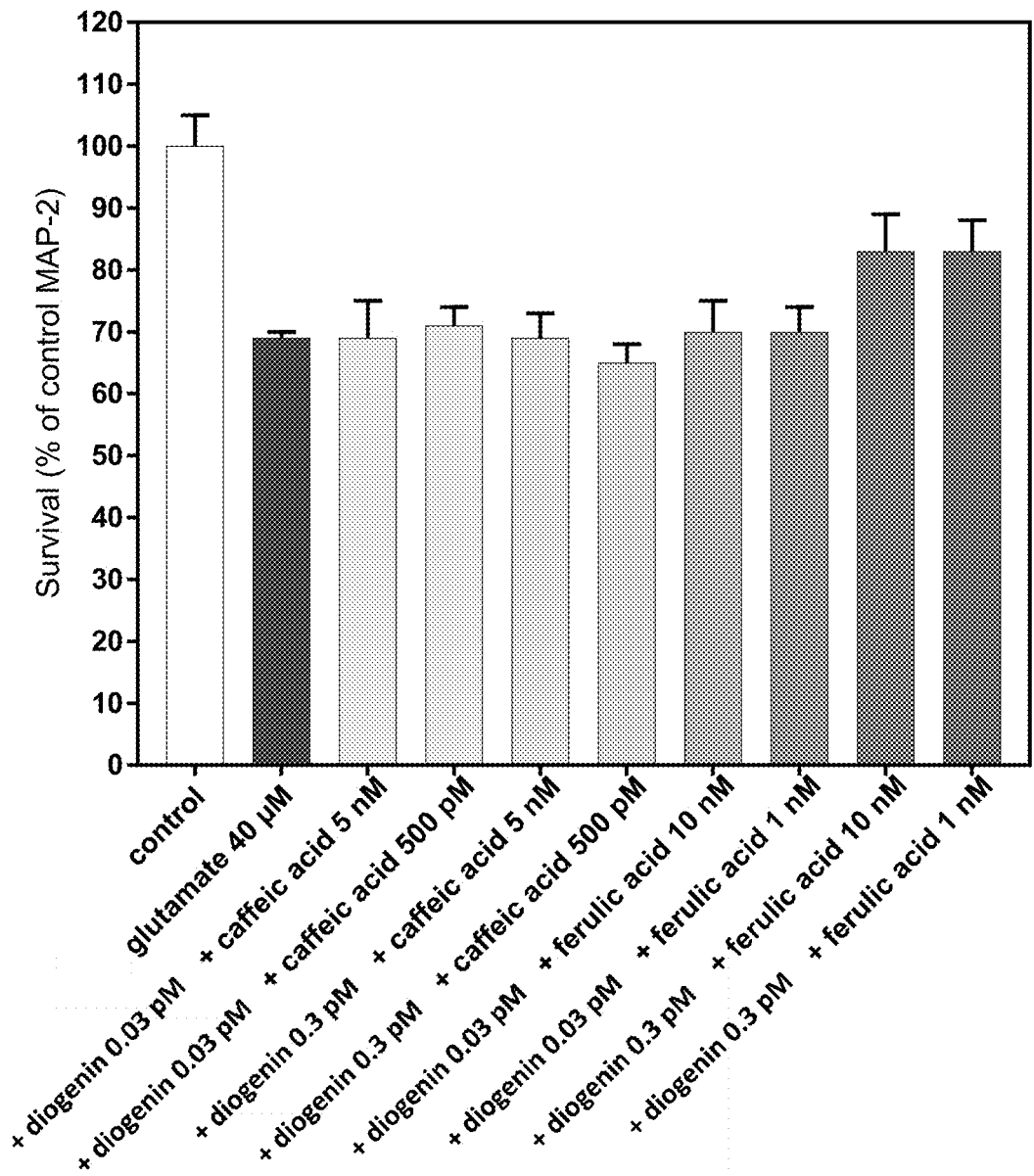
FIG. 15 illustrates the effect of Glutamate (40 µM, 20 min) in presence or absence of mix compounds (different concentrations of binary combinations: DIOSG/CAF and DIOSG/FA) on primary cortical neuron survival. Data were expressed as percentage of control as mean±SEM (100%=no glutamate). *p<0.05 vs glutamate (one way ANOVA followed by Dunnett's test).
Figure 16:
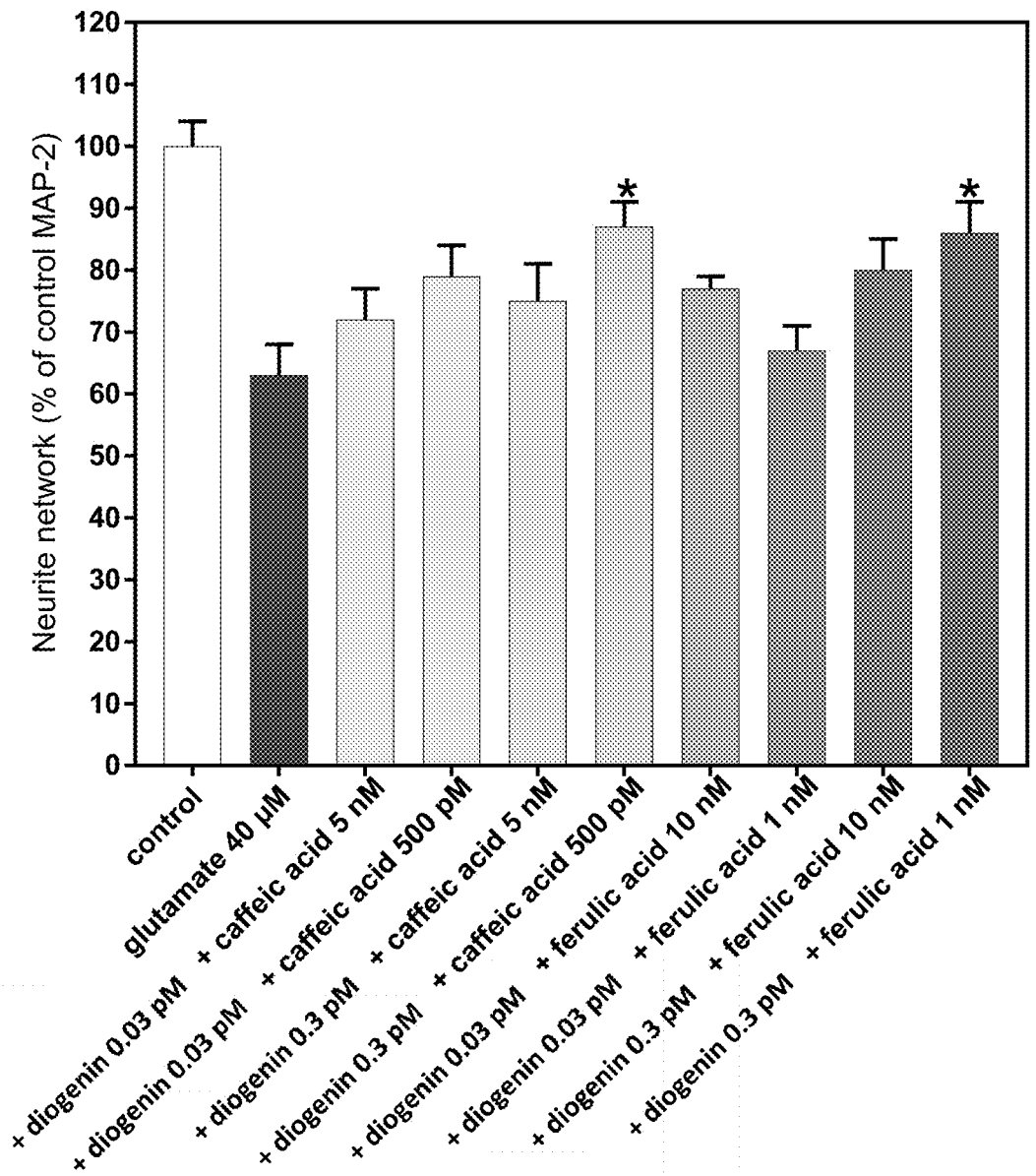
FIG. 16 illustrates the effect of Glutamate (40 µM, 20 min) in presence or absence of mix compounds (different concentrations of binary combinations: DIOSG/CAF and DIOSG/FA) on neurite network (right). Data were expressed as percentage of control as mean±SEM (100%=no glutamate). *p<0.05 vs glutamate (one way ANOVA followed by Dunnett's test).

Glutamate (40 µM, 20 min) induced a significant neuronal death (~30%). In presence of DIOS (6.3 nM-630 nM) added 1 h before the glutamate and let during the toxic application and let for the next 48 h after wash-out, a significant protective effect was observed (~80% of survival) on the neuron survival (FIG. 8A) and neuritic network (FIG. 8B).

4. Effect of Quercetin (Phenylpropanoid—Flavonoid).

The results are given in FIG. 9.

In presence of quercetin added 1 h before the glutamate and let during the toxic application and let for the next 48 h after wash-out, a significant protective effect was observed (85% of survival) at 1 and 10 nM on the neuron survival (FIG. 9A) as well as the neurite network (FIG. 9B) at 100 nM and 1 µM.

5. Effect of Catechin (Phenylpropanoid—Flavonoid).

The results are given in FIG. 10.

Glutamate (40 µM, 20 min) induced a significant neuronal death (~30%). In presence of CAT (1 nM-1 µM) added 1 h before the glutamate and let during the toxic application and let for the next 48 h after wash-out, a protective effect was observed (~80% of survival) on the neuron survival (FIG. 10A) and neuritic network (FIG. 10B) with a significant protective effect between 100 nM and 1 µM for neuron survival.

6. Effect of Caffeic Acid (CAF, Phenylpropanoid—Hydroxycinnamic Acid).

The results are given in FIG. 11.

Glutamate (40 µM, 20 min) induced a significant neuronal death (~30%). In presence of CAT (500 nM-5 µM) added 1 h before the glutamate and let during the toxic application and let for the next 48 h after wash-out, a protective effect was observed (~80% of survival) on the neuron survival (FIG. 11A) and neuritic network (FIG. 11B) with a significant protective effect between 500 nM and 5 µM for neuritic network.

7. Effect of Coumaric Acid (COU, Phenylpropanoid—Hydroxycinnamic Acid).

The results are given in FIG. 12.

Glutamate (40 µM, 20 min) induced a significant neuronal death (~30%). In presence of COU (100 nM-1 µM) added 1 h before the glutamate and let during the toxic application and let for the next 48 h after wash-out, a protective effect was observed (~80% of survival) on the neuron survival (FIG. 12A) and neuritic network (FIG. 12B) with a significant protective effect at 100 nM for neuron survival.

8. Effect of Ferulic Acid (FA).

The results are given in FIG. 13.

Glutamate (40 µM, 20 min) induced a significant neuronal death (~30%). In presence of FA (1 µM-100 µM) added 1 h before the glutamate and let during the toxic application and let for the next 48 h after wash-out, a protective effect was observed (~80% of survival) on the neuron survival (FIG. 13A) and neuritic network (FIG. 13B) with a significant protective effect between 1 µM and 100 µIM for neuritic network.

9. Effect of Gallic Acid.

The results are given in FIG. 14.

Glutamate (40 µM, 20 min) induced a significant neuronal death (~30%). In presence of Gallic acid (10 µM) added 1 h before the glutamate and let during the toxic application and let for the next 48 h after wash-out, a significant protective effect was observed (~80% of survival) on the neuron survival (FIG. 14A) and neuritic network (FIG. 14B) with a significant protective effect between 10 pM and 1 µM for neuritic network.

Example 3

Neuroprotective Effects of Binary or Ternary Combinations

The neuroprotective effect on primary cortical neurons injured by glutamate exposure of a mixture of two or three molecules tested alone in example 2 was assessed according to the method given in example 1. Their synergistic effect was also evaluated.

1. Binary Combination Compositions

The following binary combination compositions at different concentrations have been tested:

Diosgenin (DIOS) as steroidal saponin in combination with caffeic acid (OAF) or ferulic acid (FA) as first polyphenolic compound; and Sarsasapogenin (SAR) as steroidal saponin in combination with caffeic acid (OAF) or ferulic acid (FA) as first polyphenolic compound.

1.1. Effect of Diosgenin (DIOS) as Steroidal Saponin in Combination with Caffeic Acid (CAF) or Ferulic Acid (FA) as First Polyphenolic Compound The results are given in FIGS. 15 and 16.

Glutamate (40 µM, 20 min) induced a significant neuronal death (~30%) and a large loss of neurite (~40%). In presence of mix compounds (binary combinations of DIOSG/CAF or DIOSG/FA) added 1 h before the glutamate and let during the toxic application and let for the next 48 h after wash-out, a protective effect was observed (~80% of survival) on the neuron survival and neuritic network for mix DIOSG/FA at concentrations 0.3 pM/10 nM and 0.3 pM/1 nM; which a significant protective effect at the same concentrations for neuritic network and for the mix DIOSG/CAF (0.3 pM/500 pM).

By combining diosgenin with caffeic acid or ferulic acid, the concentration of diosgenin has been reduced by 10-fold comparing to the concentration of diosgenin, when diosgenin is used alone.

1.2. Effect of Sarsasapogenin as Steroidal Saponin in Combination with Caffeic Acid or Ferulic Acid as First Polyphenolic Compound.

Figure 17:
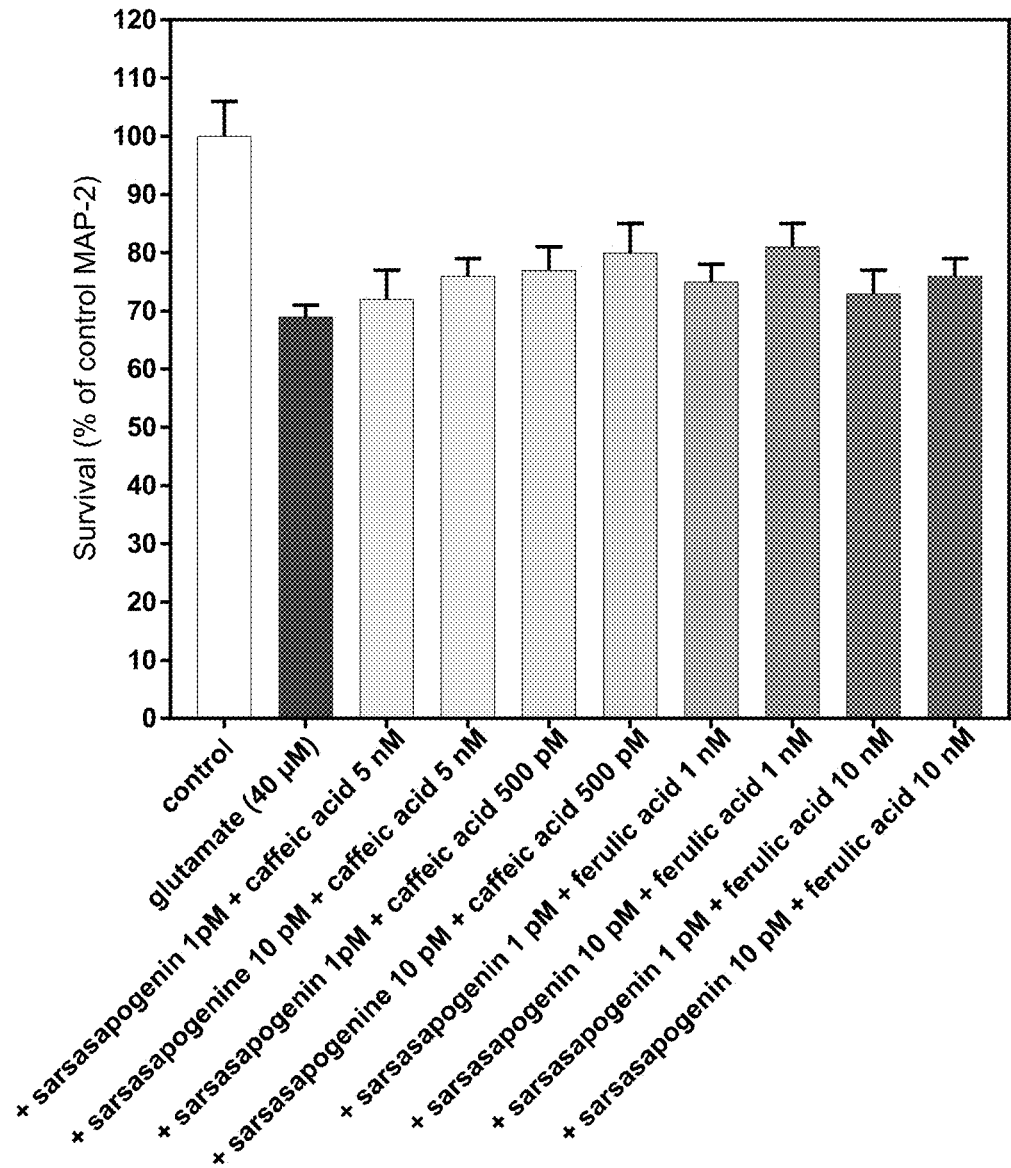
FIG. 17 illustrates the effect of Glutamate (40 µM, 20 min) in presence or absence of mix compounds (different concentrations of binary combinations: SAR/CAF and SAR/FA) on primary cortical neuron survival. Data were expressed as percentage of control as mean±SEM (100%=no glutamate). *p<0.05 vs glutamate (one way ANOVA followed by Dunnett's test).
Figure 18:
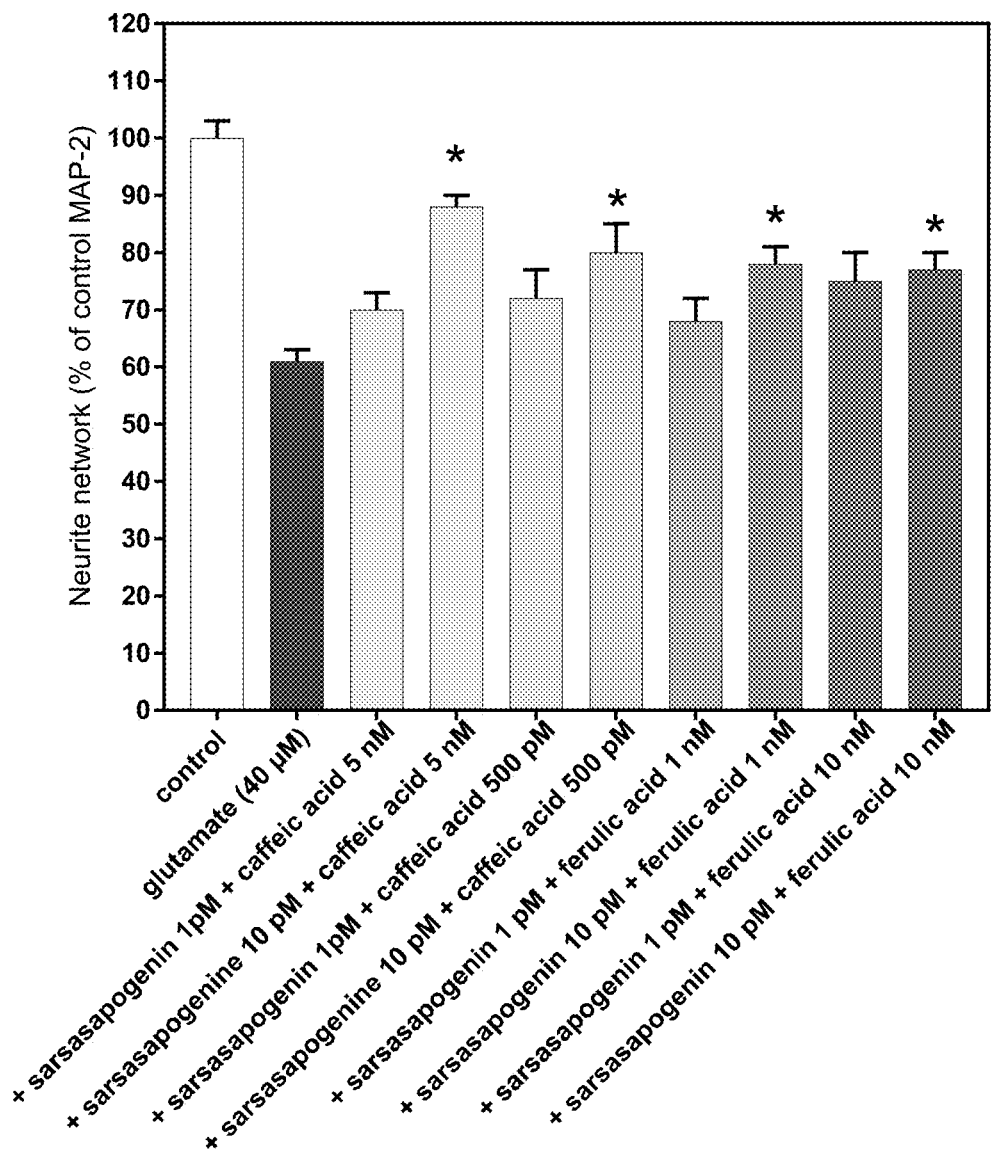
FIG. 18 illustrates the effect of Glutamate (40 µM, 20 min) in presence or absence of mix compounds (different concentrations of binary combinations: SAR/CAF and SAR/FA) on neurite network (right). Data were expressed as percentage of control as mean±SEM (100%=no glutamate). *p<0.05 vs glutamate (one way ANOVA followed by Dunnett's test).

The results are given in FIGS. 17 and 18.

Glutamate (40 μM, 20 min) induced a significant neuronal death (~30%) and a large loss of neurite (~40%). In presence of mix compounds (binary combinations of SAR/CAF or SAR/FA) added 1 h before the glutamate and let during the toxic application and let for the next 48 h after wash-out, a protective effect was observed (~80% of survival) on the neuron survival and neuritic network for mix SAR/CAF at concentrations 10 pM/5 nM and 10 pM/500 nM and mix SAR/FA at concentrations 10 pM/1 nM and 10 pM/10 nM; which a significant protective effect at the same concentrations for neuritic network.

By combining sarsasapogenin with caffeic acid or ferulic acid, the concentration of diosgenin has been reduced by 10-fold comparing to the concentration of sarsasapogenin, when sarsasapogenin is used alone.

2. Ternary Combination Compositions

The ternary combinations were prepared using:
a dose of diosgenin from 0.03 pM to 0.3 pM,
a dose of caffeic acid at a concentration from 5 nM to 50 nM, and
a dose of ferulic add at a concentration from 1 nM to 10 nM.

Figure 19:
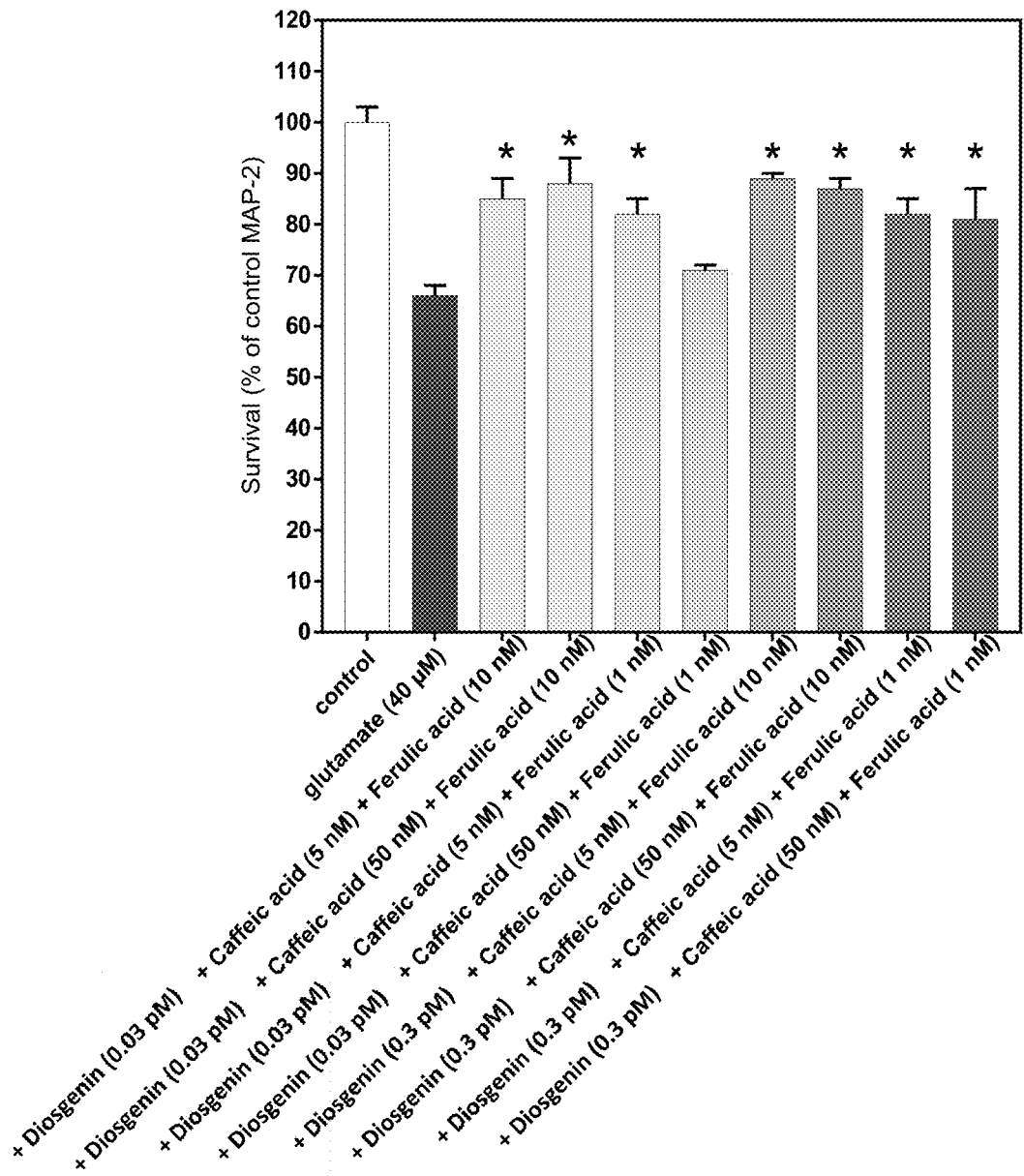
FIG. 19 illustrates the effect of Glutamate (40 µM, 20 min) in presence or absence of mix compounds (different concentrations of ternary combinations: DIOSG/CAF/FA) on primary cortical neuron survival. Data were expressed as percentage of control as mean±SEM (100%=no glutamate). *p<0.05 vs glutamate (one way ANOVA followed by Dunnett's test).
Figure 20:
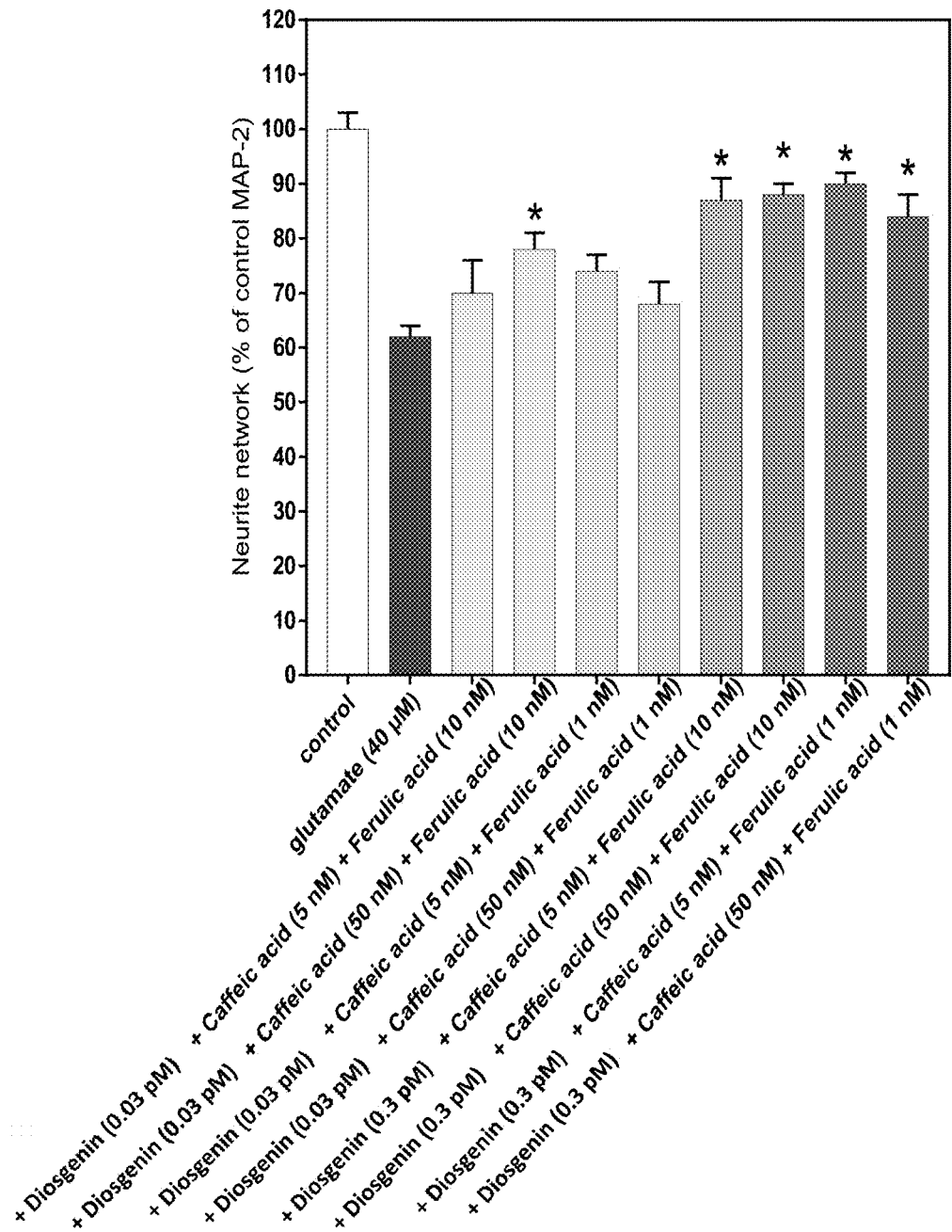
FIG. 20 illustrates the effect of Glutamate (40 µM, 20 min) in presence or absence of mix compounds (different concentrations of ternary combinations: DIOSG/CAF/FA) on neurite network. Data were expressed as percentage of control as mean±SEM (100%=no glutamate). *p<0.05 vs glutamate (one way ANOVA followed by Dunnett's test).

The results are given in FIGS. 19 and 20.

Glutamate (40 μM, 20 min) induced a significant neuronal death (~30%) and a large loss of neurite (~40%). In presence of mix compounds (ternary combination of DIOSG/CAF/FA) added 1 h before the glutamate and let during the toxic application and let for the next 48 h after wash-out, a significant protective effect was observed (~80-90% of survival) on the neuron survival and neurite network at the following concentrations:
(i) 0.03 pM/5 nM/1 nM (for neuron survival)
(ii) 0.03 pM/5 nM/10 nM (for both)
(i) 0.03 pM/50 nM/10 nM (for neuron survival)
(ii) 0.3 pM/5 nM/1 nM (for both)
(iii) 0.3 pM/5 nM/10 nM (for both)
(iv) 0.3 pM/50 nM/1 nM (for both)
(v) 0.3 pM/50 nM/10 nM (for both).

By combining DIOSG/CAF/FA, the concentration of diosgenin has been reduced by 100-fold, with a concentration at 0.03 pM, comparing to the concentration of diosgenin, when diosgenin is used alone.

The invention claimed is:

1. A combination composition comprising as active components:
a steroidal saponin of natural or synthetic origin, a pharmaceutical acceptable salt thereof, at a concentration of 0.03 pM to 0.3 pM;
caffeic acid as first polyphenolic compound at a concentration of 5 nM to 50 nM; and
ferulic acid as second polyphenolic compound at a concentration of 1 nM to 10 nM,
wherein the active components of the combination composition consist of the steroidal saponin of natural or synthetic origin, a pharmaceutical acceptable salt thereof, caffeic acid and ferulic acid,
wherein the steroidal saponin is selected from the group consisting of diosgenin, dioscin, protodioscin, sarsasapogenin, sarsaponin, smilagenin, tigogenin, laxogenin, and mixtures thereof, and
wherein said concentration of 0.03 pM to 0.3 pM of steroidal saponin is an effective concentration less than an effective concentration of steroidal saponin required without caffeic acid at said concentration of 5 nM to 50 nM and/or ferulic acid at said concentration of 1 nM to 10 nM.

2. The combination composition according to claim 1, wherein the molar ratio steroid saponin/caffeic acid/ferulic acid is from 0.03/5000/1000 0.3/5000/1000.

3. The combination composition according to claim 1 for its use as a medicament or as a nutraceutical composition.

4. The combination composition according to claim 1, further comprising at least one pharmaceutically or nutraceutically acceptable excipient.

5. The combination composition according to claim 1, wherein the combination composition is suitable for oral administration, topical administration, transdermal administration, parenteral administration and combinations thereof.

6. The combination composition according to claim 5, wherein the composition is formulated into granulates, powders, syrups, solutions, suspensions, aerosols, tablets, capsules, troches, pills, injections, suppositories, creams, drops, gels or patches.

7. The combination composition according to claim 1 for its use in inhibiting, retarding or treating a subject suffering from a neurodegenerative disease or condition.

8. The combination composition according to claim 7, wherein said neurodegenerative disease or condition is selected from the group consisting of: Alzheimer's disease (AD), senile dementia of AD type (SDAT), Parkinson's disease and all parkinsonian syndromes, Lewis body dementia, mild cognitive impairment (MCI), age-associated memory impairment (AAMI) and problem associated with ageing, non-cognitive neurodegeneration, non-cognitive neuromuscular degeneration, corticobasal ganglionic degeneration, multiple system atrophy, cerebral atrophy, olivopontocerebellar atrophy, supranuclear palsy, Niemann-Pick of type A disease, Pick diseases, traumatic neurodegeneration, Friedreich's ataxia, spinocerebellar ataxia type 2, Fahr's syndrome, Joubert syndrome, Huntington's disease, polyglutamine disease, dentatorubral atrophy, pallidoluysian atrophy, spinobulbar atrophy, myotonic dystrophy, Machado-Joseph's disease, amyotrophic lateral sclerosis (ALS), myasthenia gravis, Lambert Eaton's disease, infantile spinal amyotrophy or progressive spinal amyotrophy, motor-sensory neurodegeneration, multiple sclerosis, Guillain-Barre's syndrome, Charcot-Marie-Tooth disease (type 1 and 4), Progressive Multifocal Leukoencephalopathy (PML), leukodystrophic diseases, such as metachromatic leukodystrophy and adrenoleukodystrophy, Alexander's disease, Krabbe's disease, Zellweger's disease, Canavan disease, Pelizaeus-Merzbacher's syndrome, adrenomyeloneuropathy, neuropathies including hereditary neuropathy, diabetic neuropathy and anti-mitotic neuropathy.

9. The combination composition according to claim 8, wherein said neurodegenerative disease or condition is selected from the group consisting of Alzheimer's disease (AD), senile dementia of AD type (SDAT) and Parkinson's disease.

10. The combination composition of claim 1, wherein:
the steroidal saponin is diosgenin and is present at a concentration of from 0.03 pM to 0.3 pM, caffeic acid is at a concentration of from 5 nM to 50 nM, and ferulic acid is at a concentration of 1 nM to 10 nM, and
said concentration of 0.03 pM to 0.3 pM of diosgenin is an effective concentration less than an effective concentration of diosgenin required without caffeic acid at said concentration of 5 nM to 50 nM and/or ferulic acid at said concentration of 1 nM to 10 nM.

11. The combination composition according to claim 7, wherein:
the steroidal saponin is diosgenin and is present a concentration of from 0.03 pM to 0.3 pM, caffeic acid is at a concentration of from 5 nM to 50 nM, and ferulic acid is at a concentration of 1 nM to 10 nM, and said concentration of 0.03 pM to 0.3 pM of diosgenin is an effective concentration less than an effective concentration of diosgenin required without caffeic acid at said concentration of 5 nM to 50 nM and/or ferulic acid at said concentration of 1 nM to 10 nM.

* * * * *